United States Patent [19]

Wirth et al.

[11] Patent Number: 4,863,621
[45] Date of Patent: Sep. 5, 1989

[54] SULFUR-AND NITROGEN-CONTAINING LUBRICANT ADDITIVES

[75] Inventors: Hermann O. Wirth, Bensheim; Hans-Helmut Friedrich, Lautertal, both of Fed. Rep. of Germany

[73] Assignee: Ciba-Geigy Corporation, Ardsley, N.Y.

[21] Appl. No.: 1,783

[22] Filed: Jan. 9, 1987

[30] Foreign Application Priority Data

Jan. 10, 1986 [CH] Switzerland ............... 87/86

[51] Int. Cl.$^4$ ................. C10M 135/24; C10M 133/08
[52] U.S. Cl. .................................... 252/47.5; 252/78.1
[58] Field of Search ............ 252/47.5, 49.3, 78.1; 564/500, 501, 503, 440, 443, 340, 355

[56] References Cited

U.S. PATENT DOCUMENTS

| | | | |
|---|---|---|---|
| 2,940,933 | 6/1960 | Jezl | 252/33.6 |
| 3,454,627 | 7/1969 | James et al. | 564/500 |
| 3,590,083 | 6/1971 | Dexter et al. | 44/75 |
| 3,968,218 | 7/1976 | Bouillon et al. | 564/501 |
| 4,031,023 | 6/1977 | Musser et al. | 252/78.1 |
| 4,196,217 | 4/1980 | Rancurel et al. | 564/501 |
| 4,209,408 | 6/1980 | Hoke | 252/47 |
| 4,260,503 | 4/1981 | Michaelis | 252/47.5 |
| 4,393,026 | 7/1983 | Thompson et al. | 422/12 |
| 4,450,138 | 5/1984 | Thompson et al. | 564/153 |
| 4,519,925 | 5/1985 | Smith | 252/48.6 |
| 4,659,721 | 4/1987 | Schickaneder et al. | 514/326 |
| 4,772,405 | 9/1988 | Wirth | 564/440 |

FOREIGN PATENT DOCUMENTS

| | | | |
|---|---|---|---|
| 154721 | 9/1985 | European Pat. Off. | |
| 2606106 | 9/1976 | Fed. Rep. of Germany | 564/500 |
| 446501 | 12/1972 | U.S.S.R. | 564/501 |
| 2172284 | 9/1986 | United Kingdom | |

OTHER PUBLICATIONS

The Journal of Organic Chem., vol. 33, No. 2 (1968), pp. 523–530.

*Primary Examiner*—William R. Dixon, Jr.
*Assistant Examiner*—E. McAvoy
*Attorney, Agent, or Firm*—Stephen V. O'Brien; Harry Falber; Luther A. R. Hall

[57] ABSTRACT

Compositions containing a lubricant, a hydraulic fluid or a metal-working fluid and at least one compound of the formula I

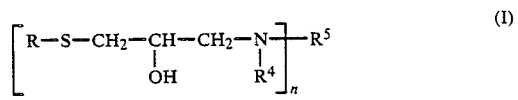

in which R, $R^4$, $R^5$ and n are as defined in claim 1, are described. The compounds of the formula I are suitable for use as anti-wear agents and as extreme-pressure additives for lubricants, hydraulic fluids and metal-working fluids. Novel compounds of the formula I are also described.

6 Claims, No Drawings

SULFUR-AND NITROGEN-CONTAINING LUBRICANT ADDITIVES

The present invention relates to lubricants, hydraulic fluids and metal-working fluids, which contain nitrogenous sulfur compounds, to the use of these compounds as additives and to novel nitrogenous sulfur compounds.

Additives are in general added to lubricants, hydraulic fluids and metal-working fluids in order to improve the properties in use. Lubricants for the transmission of relatively high forces must meet special requirements with respect to the load-carrying capacity. The adverse phenomena which would otherwise occur are greatly reduced by the addition of extreme-pressure additives and wear-reducing additives.

Sulfur-containing ammonium compounds as corrosion inhibitors are described in U.S. Patent Specification No. 4,450,138.

The present invention relates to a composition containing a lubricant, a hydraulic fluid or a metal-working fluid and at least one compound of the formula I

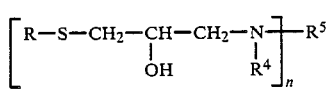     (I)

in which n is equal to 1 to 6 and R can be a radical of the formula

in which $R^1$, $R^2$ and $R^3$ independently of one another are $C_1$–$C_{21}$-alkyl and together have not more than 22 carbon atoms, and $R^2$ and $R^3$ can also be hydrogen, or in which R is $C_5$–$C_{12}$-cycloalkyl, $C_7$–$C_9$-aralkyl, unsubstituted or $C_1$–$C_4$-alkyl-substituted phenyl or naphthyl, furyl, furfuryl, thienyl, morpholinyl, imidazolyl, thiazolyl, oxazolyl, imidazolinyl, thiazolinyl, oxazolinyl, benzimidazolinyl, benzothiazolinyl or benzoxazolinyl, and in which $R^4$ is hydrogen or $C_1$–$C_{20}$-alkyl which is unsubstituted or substituted by —OH, —OCH$_3$, —CN or —N($R^6$)$_2$, and $R^6$ is unsubstituted or OH-substituted $C_1$–$C_4$-alkyl, and $R^4$ $C_1$–$C_{20}$-alkyl may be interrupted by —O—, —S— or

or $R^4$ is $C_4$–$C_{20}$-alkenyl, $C_4$–$C_{20}$-alkynyl, unsubstituted or $C_1$–$C_4$-alkyl-substituted $C_6$–$C_{12}$-cycloalkyl, $C_6$-, $C_{10}$- or $C_{14}$-aryl which is unsubstituted or substituted by one or two $C_1$–$C_4$-alkyl or —CF$_3$, one or two OH groups or one or two —N($R^7$) ($R^8$), and $R^7$ is hydrogen or $C_1$–$C_4$-alkyl and $R^8$ is $C_1$–$C_4$-alkyl or $C_6$- or $C_{10}$-aryl, or in which $R^4$ is anthraquinonyl, $C_1$–$C_{10}$-heteroaryl which is unsubstituted or substituted by —OH or $C_1$–$C_4$-alkyl, a nonaromatic $C_2$–$C_5$-heterocyclic ring or $C_7$–$C_{14}$-aralkyl which is unsubstituted or substituted by —OH, $C_1$–$C_4$-alkoxy or —N($R^6$)$_2$ or $R^4$ is —CH$_2$—CH(OH)—CH$_2$—S—R, and $R^5$ is $C_4$–$C_{20}$-alkyl which is unsubstituted or substituted by —OCH$_3$, —CN or —N($R^6$)$_2$, $R^6$ being as defined above, and which may be interrupted by —O—, —S— or

or $R^5$ is $C_1$–$C_{20}$-alkyl which is substituted by N($R^6$) (tolyl) or $C_1$–$C_{10}$-heteroaryl, or $R^5$ is unsubstituted $C_4$–$C_{20}$-alkenyl or $C_3$–$C_{20}$-alkenyl substituted by one or more —CN, $C_4$–$C_{20}$-alkynyl, unsubstituted or $C_1$–$C_4$-alkyl-substituted $C_6$–$C_{12}$-cycloalkyl or $C_6$–$C_1C_{10}$- or $C_{14}$-aryl which is unsubstituted or substituted by one or more $C_1$–$C_4$-alkyl groups which may be interrupted by —NH— or —N($R^6$)—, one or more $C_1$–$C_4$-alkoxy, $C_1$–$C_4$-alkylthio and/or OH groups, one or more —NO$_2$, —CF$_3$ and/or —CN, hydroxyethoxy, phenoxy, ureido, carbamoyl, sulfamoyl, benzeneazo, tolueneazo, anilinocarbonyl, anilinosulfonyl, —S—CH$_2$—CH(OH)—CH$_2$—S—R and/or one or two —N($R^7$) ($R^8$), $R^7$ and $R^8$ being as defined above and $R^8$ additionally also being acetyl or methoxyphenyl, or in which $R^5$ is anthraquinonyl, hydroxyanthraquinonyl, $C_1$–$C_{10}$-heteroaryl which is unsubstituted or substituted by —OH, phenyl or $C_1$–$C_4$-alkyl, or $C_7$–$C_{14}$-aralkyl which is unsubstituted or substituted by —OH, one or more $C_1$–$C_4$-alkoxy groups or by —N($R^6$)$_2$, $R^6$ being as defined above, or $R^5$ is —CH$_2$—CH(OH)CH$_2$—S—R or $R^5$ is a divalent $C_2$–$C_{12}$-aliphatic radical which is derived from a $C_2$–$C_{12}$-alkane disubstituted by —NH$_2$ and can be unsubstituted or substituted by —OH, —OCH$_3$ or —N($R^6$)$_2$ and may be interrupted by —O—, —S— or —N($R^9$)—, $R^9$ being unsubstituted or OH-substituted $C_1$–$C_4$-alkyl or —CH$_2$—CH(OH)—CH$_2$—S—R, or $R^5$ is a divalent to tetravalent $C_6$–$C_{12}$-cycloaliphatic radical which is derived from a $C_6$–$C_{12}$-cycloalkane disubstituted to tetrasubstituted by —NH$_2$ and can be unsubstituted or substituted by $C_1$–$C_4$-alkyl, or $R^5$ is a radical of the formula

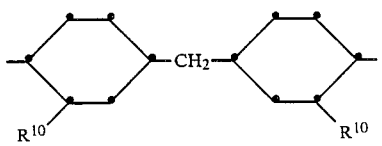

in which $R^{10}$ is hydrogen or $C_1$–$C_4$-alkyl, or $R^5$ is a radical of the formula

or a divalent or trivalent $C_6$-, $C_{10}$- or $C_{14}$-aromatic radical which is derived from a $C_6$-, $C_{10}$- or $C_{14}$-aromatic disubstituted or trisubstituted by —NH$_2$ and can be unsubstituted or substituted by —OH, —NO$_2$ or $C_1$–$C_4$-alkyl, or $R^5$ is anthraquinonylene, 2,3-dihydroanthraquinonylene or a radical of the formula

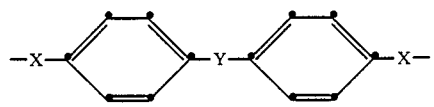

in which X is —CH$_2$— or a direct bond and Y is —CH$_2$—, —C(C$_6$H$_5$)—H—, —S—S—, —NH— or a direct bond, or R$^5$ is a divalent or trivalent C$_2$–C$_{10}$-heteroaromatic radical which is derived from a C$_2$–C$_{10}$-heteroaromatic ring disubstituted or trisubstituted by —NH$_2$ and can be unsubstituted or substituted by —OH or C$_6$- or C$_{10}$-aryl, or R$^5$ is a divalent C$_7$–C$_{14}$-araliphatic radical which is derived from a C$_7$–C$_{14}$-aralkane disubstituted by —NH$_2$, or R$^4$ and R$^5$ together with the N atom to which they are linked form a C$_1$–C$_7$-azacyclic ring which can be aromatic or non-aromatic and may contain one or more N, O or S atoms, the N atom being unsubstituted or substituted by C$_1$–C$_4$-alkyl which in turn can be substituted by —OH, and the C$_1$–C$_7$-azacyclic ring can be unsubstituted or substituted on one C atom by C$_1$–C$_4$-alkyl, =O or =S, or R$^4$ and R$^5$ together with the N atom to which they are linked are 2,2,4-trimethyl-1,2-dihydroquinolyl, a part of a C$_1$–C$_7$-azacyclic divalent to hexavalent ring or a radical of the formulae

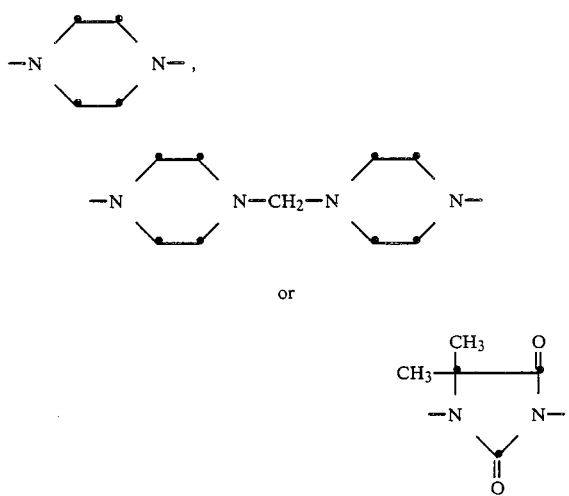

or

A radical R of the formula

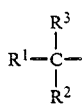

can be, for example, R$^1$CH$_2$—,

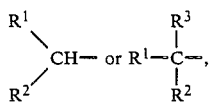

R$^1$, R$^2$ and R$^3$ each being C$_1$–C$_{21}$-alkyl. C$_1$–C$_{21}$-Alkyl is a straight-chain or branched substituent, for example methyl, ethyl, n-propyl, isopropyl, n-butyl, isobutyl, sec.-butyl, tert.-butyl, a straight-chain or branched pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl or heneicosyl.

in which R$^1$, R$^2$ and R$^3$ together with the C atom to which they are linked form C$_4$–C$_{22}$-alkyl, is preferred, but none of these substituents R$^1$, R$^2$ and R$^3$ may then by hydrogen; in this case, C$_4$–C$_{16}$-alkyl is then particularly preferred, in particular tert.-butyl, tert.-pentyl, tert.-nonyl or tert.-dodecyl (ex Phillips Petroleum), and very particularly tert.-butyl or tert.-nonyl are preferred, and tert.-dodecyl is here to be understood, for example, as a radical such as is described for tertiary dodecylmercaptan in "Ullmanns Enzyklopadie der technischen Chemie [Ullmann's Encyclopaedia of Industrial Chemistry]", 4th edition, volume 23, pages 181–182, Verlag Chemie, Weinheim.

A C$_5$–C$_{12}$-cycloalkyl radical R is, for example, cyclopentyl, cyclohexyl, cycloheptyl, cyclooctyl, cyclononyl, cyclodecyl, cycloundecyl or cyclododecyl, preferably cyclohexyl.

A C$_7$–C$_9$-aralkyl radical R is, for example, benzyl, 1- or 2-phenylethyl, 3-phenylpropyl or 2-phenylisopropyl, preferably benzyl.

In a phenyl or naphthyl radical R substituted by C$_1$–C$_4$-alkyl, phenyl or naphthyl can be monosubstituted to trisubstituted, but preferably monosubstitued; C$_1$–C$_4$-alkyl is methyl, ethyl, n-propyl, isopropyl, n-butyl, isobutyl, sec.-butyl or tert.-butyl.

A C$_1$–C$_{20}$-alkyl radical R$^4$ is a straight-chain or branched alkyl radical, for example, methyl, ethyl, n-propyl, isopropyl, n-butyl, isobutyl, sec.-butyl, tert.-butyl, or straight-chain or branched pentyl, hexyl, heptyl, octyl, nonyl, decyl, undecyl, dodecyl, tridecyl, tetradecyl, pentadecyl, hexadecyl, heptadecyl, octadecyl, nonadecyl or eicosyl; isopropyl, tert.-butyl, isooctyl, 2-ethylhexyl, tert.-nonyl, tert.-dodecyl or tert.-tridecyl are preferred. Isooctyl is here understood as a radical which is derived from isooctyl alcohol and is a mixture of octyl radicals with different branching; the definitions given above are to apply to tert.-nonyl and tert.-dodecyl.

In a C$_1$–C$_{20}$-alkyl radical R$^4$ substituted by —OH, —OCH$_3$, —CN or N(R$^6$)$_2$, C$_1$–C$_{20}$-alkyl can be monosubstituted or polysubstituted, but at most disubstituted in the case of substitution by —OH, substitution being possible in any position but preferably terminal in the case of monosubstitution.

In a C$_1$–C$_{20}$-alkyl radical R$^4$ which is interrupted by —O—, —S— or

the heteroatoms can be in any possible position, and the C$_1$–C$_{20}$-alkyl radical can be interrupted once or several times, it being possible for the heteroatoms to be identical or different.

C$_4$–C$_{20}$-Alkenyl radicals R$^4$ or R$^5$ are straight-chain or branched alkenyl radicals which contain one or more, but preferably one double bond, for example n-butenyl, i-pentenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl or eicosenyl.

$C_4$–$C_{20}$-Alkynyl radicals $R^4$ or $R^5$ are straight-chain or branched alkynyl radicals which contain one or more, but preferably one triple bond, for example N-butynyl, n-pentynl, 1,1-dimethyl-prop-2-yn-1-yl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl or eicosynyl.

$C_6$–$C_{12}$-Cycloalkyl radicals $R^4$ or $R^5$ are, for example, cyclohexyl, cycloheptyl, cyclooctyl, cyclononyl, cyclodecyl, cycloundecyl or cyclododecyl, preferably cyclohexyl.

$C_1$–$C_4$-Alkyl-substituted $C_6$–$C_{12}$-cycloalkyl radicals $R^4$ or $R^5$ are monosubstituted or polysubstituted, but preferably monosubstituted $C_6$–$C_{12}$-cycloalkyl, $C_1$–$C_4$-alkyl being, for example, methyl, ethyl, n-propyl, isopropyl, n-butyl, isobutyl, sec.-butyl or tert.-butyl.

$C_6$-, $C_{10}$- or $C_{14}$-aryl radicals $R^4$ or $R^5$ are, for example phenyl, naphthyl, anthryl or phenanthryl.

In $C_6$-, $C_{10}$ or $C_{14}$-aryl radicals $R^4$ or $R^5$ substituted by $C_1$–$C_4$-alkyl, $C_1$–$C_4$-alkoxy and/or $C_1$–$C_4$-alkylthio, the aryl radical can be monosubstituted or polysubstituted but preferably monosubstituted to disubstituted; $C_1$–$C_4$-alkyl in this case is methyl, ethyl, n-propyl, isopropyl, n-butyl, isobutyl, sec.-butyl or tert.-butyl.

In $C_6$-, $C_{10}$ or $C_{14}$-aryl radicals $R^4$ or $R^5$ substituted by —$CF_3$, —OH and/or —$N(R^7)(R^8)$, the aryl radical can be monosubstituted or disubstituted, but preferably monosubstituted.

In $C_1$–$C_{10}$-heteroaryl radicals $R^4$ or $R^5$, the heteroaryl radical can contain one or more heteroatoms and may be benzo-fused, the heteroatoms being, for example, nitrogen, oxygen or sulfur atoms. Examples of $C_1$–$C_{10}$-heteroaryl are tetrazolyl, triazolyl, imidazolyl, pyrazolyl, pyrryl, thiazolyl, thiadiazolyl, thiatriazolyl, thienyl, furyl, oxazolyl, oxadiazolyl, oxatriazolyl, pyridyl, pyridanzinyl, pyrimidyl, pyrazinyl, triazinyl, tetrazinyl, benzotriazolyl, benzothiadiazolyl, purinyl, indolyl, carbazolyl or pteridinyl, and preferably tetrazolyl, triazolyl, imidazolyl, pyrazolyl, thiazolyl, thiadiazolyl, or pyridyl.

$C_1$–$C_{10}$-Heteroaryl radicals $R^4$ or $R^5$ substituted by —OH, phenyl and/or $C_1$–$C_4$-alkyl can be monosubstituted or polysubstituted, but are preferably monosubstituted; $C_1$–$C_4$-alkyl is, for example, methyl, ethyl, n-propyl, isopropyl, n-butyl, isobutyl, sec.-butyl or tert.-butyl.

A non-aromatic $C_2$–$C_5$-heterocyclic radical $R_4$ is, for example, dihydrooxazolyl, dihydrothiazolyl, pyranyl, thietanyl, oxetanyl, morpholinyl, piperidyl or piperazinyl.

$C_7$–$C_{14}$-Aralkyl radicals $R^4$ or $R^5$ are, for example, benzyl, 1- or 2-phenylethyl, 3-phenylpropyl, 2-phenylisopropyl, 2-phenylhexyl, naphthylmethyl or naphthylbutyl, but preferably benzyl or 2-phenylethyl.

$C_7$–$C_{14}$-Aralkyl radicals $R^4$ or $R^5$ substituted by —OH, $C_1$–$C_4$-alkoxy or —$N(R^6)_2$ can, for example, be monsubstituted to trisubstituted; $C_1$–$C_4$-alkoxy is, for example, methoxy, ethoxy, n-propoxy, isopropoxy, n-butoxy, isobutoxy, sec.-butoxy or tert.-butoxy.

A $C_4$–$C_{20}$-alkyl radical $R^5$ is a straight-chain or branched alkyl radical, for example n-butyl, isobutyl, sec.-butyl, tert.-butyl, straight-chain or branched pentyl, hexyl, heptyl, octyl, nonyl, decyl, undecyl, dodecyl, tridecyl, tetradecyl, pentadecyl, hexadecyl, heptadecyl, octadecyl, nonadecyl or eicosyl.

In a $C_4$–$C_{20}$-alkyl radical $R^5$ substituted by —$OCH_3$, —CN or $N(R^6)_2$, the $C_4$–$C_{20}$-alkyl can be monosubstituted or polysubstituted, substitution being possible in any position but preferably being terminal in the case of monosubstitution.

In a $C_4$–$C_{20}$-alkyl radical $R^5$ interrupted by —O—, —S— or

the heteroatoms can be in any position and the $C_4$–$C_{20}$-alkyl radical can be interrupted once or several times, it being possible for the heteroatoms to be identical or different.

A $C_1$–$C_{20}$-alkyl radical $R^5$ substituted by $N(R^6)$—(tolyl) or by $C_1$–$C_{10}$-heteroaryl is a monosubstituted or disubstituted, preferably monosubstituted, straight-chain or branched $C_1$–$C_{20}$-alkyl, substitution being possible in any position but preferably being terminal in the case of monosubstitution.

A CN-substituted $C_3$–$C_{20}$-alkenyl radical $R^5$ can be monosubstituted or polysubstituted, preferably polysubstituted. $C_3$–$C_{20}$-alkenyl is a straight-chain or branched alkenyl radical which contains one or more, preferably one double bond. In particular, this is a 1,1,3-tricyano-prop-1-en-2-yl radical.

In a $C_6$-, $C_{10}$- or $C_{14}$-aryl radical $R^5$ substituted by $C_1$–$C_4$-alkyl groups interrupted by —NH— or —$N(R^6)$—, $C_1$–$C_4$-alkyl is preferably interrupted by one —NH— or —$N(R^6)$— and is, for example, N-methyl-aminomethylphenyl or N-dimethyl-aminomethylphenyl, which are also preferred.

$C_6$-, $C_{10}$- or $C_{14}$-aryl radicals $R^5$ substituted by $NO_2$, CN, hydroxyethoxy, phenoxy, ureido, carbamoyl, sulfamoyl, benzeneazo, tolueneazo, anilinocarbonyl, anilinosulfonyl and/or —S—$CH_2$—CH(OH)—$CH_2$—S—R can be monosubstituted to polysubstituted, preferably monosubstituted to trisubstituted. Preferably, the aryl radicals are phenyl or naphthyl, especially phenyl.

In a divalent $C_2$–$C_{12}$-aliphatic radical $R^5$ which is derived from a $C_2$–$C_{12}$-alkane disubstituted by —$NH_2$ and which can be prepared, for example, by adding $NH_3$ to $C_2$–$C_{12}$-olefins, the $C_2$–$C_{12}$-alkane can be straight-chain or branched, so that it can be, for example, ethylene, propylene, trimethylene, tetramethylene, pentamethylene, 2,2-dimethyl-1,3-trimethylene, hexamethylene, heptamethylene, octamethylene, nonamethylene, decamethylene, undecamethylene, dodecamethylene or 2,5-hexanediyl.

In a divalent $C_2$–$C_{12}$-aliphatic radical $R^5$ substituted by —OH, —$OCH_3$ or —$N(R^6)_2$, substitution in any position is possible.

In a divalent $C_2$–$C_{12}$-aliphatic radical $R^5$ interrupted by —O—, —S— or —$N(R^9)$—, the heteroatoms can be in any position and the $C_2$–$C_{12}$-aliphatic radical can be interrupted once or several times, it being possible for the heteroatoms to be identical or different; an example is 3-thiapentamethylene.

A divalent to tetravalent $C_6$–$C_{12}$-cycloaliphatic radical $R^5$ which is derived from a $C_6$–$C_{12}$-cycloalkane disubstituted to tetrasubstituted by —$NH_2$ and which can be prepared, for example, by adding $NH_3$ to $C_6$–$C_{12}$-cycloalkenes, is, for example, 1,4-cyclohexanediyl, 1,2-cyclohexanediyl, 1,3-cycloheptanediyl, 1,5-cyclooctanediyl, 1,3,5,7-cyclooctanetetrayl, 1,3-cyclononanediyl, 1,6-cyclodecanediyl, 1,4,8-cycloundecanetriyl or 1,4,7,10-cyclododecanetetrayl. Divalent $C_6$–$C_{12}$-cycloaliphatic radicals are preferred.

A divalent to tetravalent $C_1$–$C_4$-alkyl-substituted $C_6$–$C_{12}$-cycloaliphatic radical $R^5$ can be monosubstituted or polysubstituted, preferably monosubstituted or disubstituted, and the substitution can be in any position.

A divalent or trivalent $C_6$-, $C_{10}$- or $C_{14}$-aromatic radical $R^5$ which can be obtained, for example, by reduction of the corresponding nitroaromatics, is, for example, phenylene, naphthylene, anthrylene or 1,3,5-benzene-triyl, and preferably phenylene or naphthylene.

A divalent or trivalent $C_6$-, $C_{10}$- or $C_{14}$-aromatic radical $R^5$ substituted by —OH or $C_1$–$C_4$-alkyl can be monosubstituted or polysubstituted, preferably monosubstituted or disubstituted, and the substitution can be in any position.

In a divalent or trivalent $C_2$–$C_{10}$-heteroaromatic radical $R^5$ which is derived from a $C_2$–$C_{10}$-heteroaromatic which is disubstituted or trisubstituted by —$NH_2$ and which can be obtained, for example, by reduction of the corresponding nitroaromatics, the heteroaryl polyradical can contain one or more heteroaroms, examples of the heteroatoms being nitrogen, oxygen or sulfur atoms. Examples of such radicals are 2,5-pyrrole-diyl, 3,5-triazole-diyl, 3,4-pyrazole-diyl, 2,4-thiazole-diyl, 2,6-pyridine-diyl, 4,6-pyrimidine-diyl or 2,4,6-triazine-triyl, the said radicals, in particular 2,4,6-triazine-triyl, being preferred.

A divalent or trivalent $C_2$–$C_{10}$-heteroaromatic radical $R^5$ substituted by —OH or $C_6$- or $C_{10}$-aryl can be monosubstituted or polysubstituted, preferably monosubstituted or disubstituted, and the substitution can be in any position.

A divalent $C_7$–$C_{14}$-araliphatic radical $R^5$ which is derived from a $C_7$–$C_{14}$-aralkane disubstituted by —$NH_2$ and which can be prepared, for example, by addition of $NH_3$ to a $C_7$–$C_{14}$-aralkene is, for example,

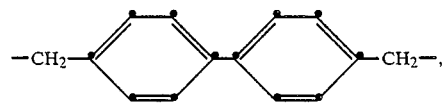

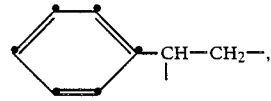

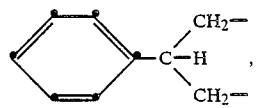

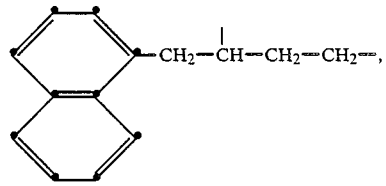

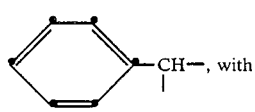, with

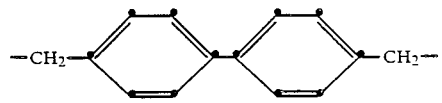

being preferred.

If $R^4$ and $R^5$ together with the N atom to which they are linked form a $C_1$–$C_7$-azacyclic ring which can be aromatic or non-aromatic and may contain one or more N, O or S atoms, it being possible for the N atom to be unsubstituted or substituted by $C_1$–$C_4$-alkyl which in turn can be substituted by OH, and it being possible for the $C_1$–$C_7$-azacyclic ring to be substituted on one C atom by $C_1$–$C_4$-alkyl, =O or =S, these are, for example,

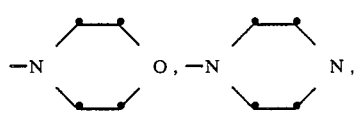

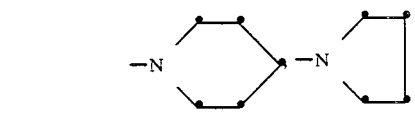

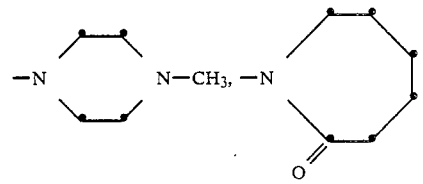

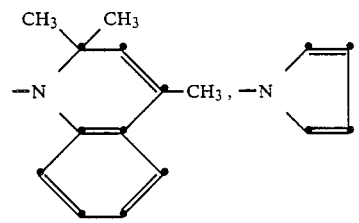

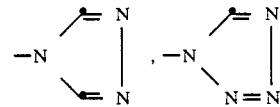

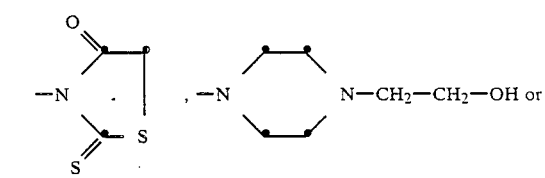

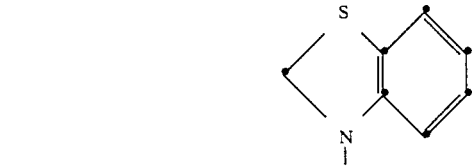

the examples being preferred.

If $R^4$ and $R^5$ together form a part of a $C_1$-$C_7$-azacyclic divalent to hexavalent ring, they are, for example,

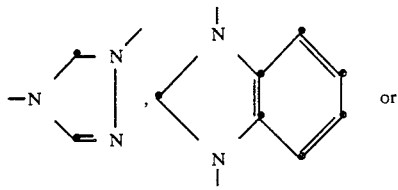 or

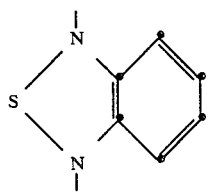

$C_1$-$C_4$-Alkyl radicals $R^6$, $R^7$, $R^8$, $R^9$ or $R^{10}$ are methyl, ethyl, n-propyl, isopropyl, n-butyl, isobutyl, sec.-butyl or tert.-butyl.

OH-substituted $C_1$-$C_4$-alkyl radicals $R^6$ or $R^9$ can be monosubstituted or polysubstituted, but preferably monosubstituted. For example, these are 2-hydroxyethyl or 2,3-dihydroxypropyl, preferably 2-hydroxyethyl.

A $C_6$- or $C_{10}$-aryl radical $R^8$ is phenyl or naphthyl.

A special embodiment of the composition according to the invention is that in which n in the formula I is 1.

A further embodiment of the composition according to the invention is that in which n is the formula I is 2 to 6, but preferably 2.

A composition is preferred which contains a lubricant, a hydraulic fluid or a metal-working fluid and at least one compound of the formula I, wherein R in the formula I is a radical of the formula

in which $R^1$, $R^2$ and $R^3$ independently of one another are $C_1$-$C_{18}$-alkyl and do not have more than 22 carbon atoms in total, and $R^2$ and $R^3$ can also be hydrogen, or wherein R is $C_5$-$C_6$-cycloalkyl, benzyl, unsubstituted or $C_1$-$C_4$-alkyl-substituted phenyl or unsubstituted naphthyl.

A composition is particularly preferred which contains a lubricant, a hydraulic fluid or a metal-working fluid and at least one compound of the formula I, wherein R in the formula I is a radical of the formula

in which $R^1$, $R^2$ and $R^3$ together with the carbon atom to which they are linked form $C_4$-$C_{16}$-alkyl, in which case none of these substituents $R^1$, $R^2$ and $R^3$ may be hydrogen, or wherein R is cyclohexyl, benzyl, unsubstituted or $C_1$-$C_4$-alkylsubstituted phenyl or unsubstituted naphthyl.

A composition is also of interest which contains a lubricant, a hydraulic fluid or a metal-working fluid and at least one compound of the formula I, wherein R in the formula I is a radical of the formula

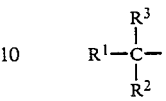

in which $R^1$ is $C_1$-$C_{12}$-alkyl and $R^2$ and $R^3$ are hydrogen.

A composition is also of special interest which contains a lubricant, a hydraulic fluid or a metal-working fluid and at least one compound of the formula I, wherein R in the formula I is a radical of the formula

in which $R^1$ and $R^2$ independently of one another are $C_1$-$C_{12}$-alkyl and together with the carbon atom to which they are linked form $C_3$-$C_{14}$-alkyl and $R^3$ is hydrogen.

A composition is especially preferred which contains a lubricant, a hydraulic fluid or a metal-working fluid and at least one compound of the formula I, wherein $R^4$ in the formula I is hydrogen, $C_6$-, $C_{10}$- or $C_{14}$-aryl which is unsubstituted or substituted by one or two $C_1$-$C_4$-alkyl or —$CF_3$, one or two OH groups or one or two —$N(R^7)(R^8)$ and $R^7$ is hydrogen or $C_1$-$C_4$-alkyl and $R^8$ is $C_1$-$C_4$-alkyl or $C_6$- or $C_{10}$-aryl or wherein $R^4$ is anthraquinonyl or is $C_1$-$C_{10}$-heteroaryl which is unsubstituted or substituted by —OH or $C_1$-$C_4$-alkyl, and $R^5$ is $C_6$-, $C_{10}$- or $C_{14}$-aryl which is unsubstituted or substituted by one or more $C_1$-$C_4$-alkyl groups which may be interrupted by —NH— or —$N(R^6)$—, one or more $C_1$-$C_4$-alkoxy, $C_1$-$C_4$-alkylthio and/or or OH groups, one or more —$NO_2$, —$CF_3$ and/or —CN, hydroxyethoxy, phenoxy, ureido, carbamoyl, sulfamoyl, benzeneazo, tolueneazo, anilinocarbonyl, anilinosulfonyl, —S—$CH_2$—CH(OH)—$CH_2$—S—R and/or one or two —$N(R^7)(R^8)$, $R^7$ and $R^8$ being as defined above and $R^8$ also being acetyl or methoxyphenyl, or wherein $R^5$ is antraquinonyl, hydroxyanthraquinonyl or is $C_1$-$C_{10}$-heteroaryl which is unsubstituted or substituted by —OH, phenyl and/or $C_1$-$C_4$-alkyl or $R^5$ is a divalent or trivalent $C_6$-, $C_{10}$- or $C_{14}$-aromatic radical which is derived from a $C_6$-, $C_{10}$- or $C_{14}$-aromatic disubstituted or trisubstituted by —$NH_2$ and can be unsubstituted or substituted by —OH, $NO_2$ or $C_1$-$C_4$-alkyl, or $R^5$ is anthraquinonylene, 2,3-dihydroanthraquinonylene or a radical of the formula

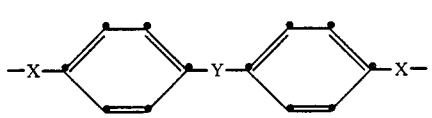

in which X is a direct bond and Y is —$CH_2$—, —$C(C_6H_5)H$—, —S—S—, —NH— or a direct bond, or $R^5$ is a divalent or trivalent $C_2$-$C_{10}$-heteroaromatic radical which is derived from a $C_2$–$C_{10}$-heteroaromatic disubstituted or trisubstituted by —$NH_2$ and is unsubstituted or substituted by —OH or $C_6$- or $C_{10}$-aryl, or $R^4$ and $R^5$ together with the N atom to which they are linked form a $C_1$–$C_7$-azacyclic ring which is aromatic and may contain one or more N, O or S atoms, or $R^4$ and $R^5$ together with the N atom to which they are linked are a 2,2,4-trimethyl-1,2-dihydroquinolyl radical.

The invention also relates to novel compounds of the formula Ia

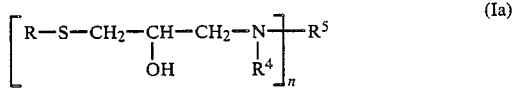

in which n is 1 to 6 and R is a radical of the formula

in which $R^1$, $R^2$ and $R^3$ together with the carbon atom to which they are linked form $C_5$–$C_{20}$-alkyl and none of these substituents $R^1$, $R^2$ and $R^3$ may be hydrogen, and wherein $R^4$ is hydrogen or $C_1$–$C_{20}$-alkyl which is unsubstituted or substituted by —OH, —$OCH_3$, —CN or —$N(R^6)_2$, and $R^6$ is unsubstituted or OH-substituted $C_1$–$C_4$-alkyl, and $C_1$–$C_{20}$-alkyl $R^4$ may be interrupted by —O—, —S— or

or $R^4$ is $C_4$–$C_{20}$-alkenyl, $C_4$–$C_{20}$-alkynyl, unsubstituted or $C_1$–$C_4$-alkyl-substituted $C_6$–$C_{12}$-cycloalkyl, $C_6$-, $C_{10}$- or $C_{14}$-aryl which is unsubstituted or substituted by one or two $C_1$–$C_4$-alkyl or —$CF_3$, one or two OH groups or one or two —$N(R^7)(R^8)$, and $R^7$ is hydrogen or $C_1$–$C_4$-alkyl and $R^8$ is $C_1$–$C_4$-alkyl or $C_6$- or $C_{10}$-aryl, or in which $R^4$ is anthraquinonyl, $C_1$–$C_{10}$-heteroaryl which is unsubstituted or substituted by —OH or $C_1$–$C_4$-alkyl, a non-aromatic $C_2$–$C_5$-heterocyclic ring or $C_7$–$C_{14}$-aralkyl which is unsubstituted or substituted by —OH, $C_1$–$C_4$-alkoxy or —$N(R^6)_2$ or $R^4$ is —CH(OH)—$CH_2$—S—R, and $R^5$ is $C_5$–$C_{20}$-alkyl which is unsubstituted or substituted by —$OCH_3$, —CN or —$N(R^6)_2$, $R^6$ being as defined above, and which may be interrupted by —O—, —S— or

or $R^5$ is $C_1$–$C_{20}$-alkyl which is substituted by $N(R^6)$(tolyl) or $C_1$–$C_{10}$-heteroaryl, or $R^5$ is unsubstituted $C_4$–$C_{20}$-alkenyl or $C_3$–$C_{20}$-alkenyl substituted by one or more —CN, $C_4$–$C_{20}$-alkynyl, unsubstituted or $C_1$–$C_4$-alkyl-substituted $C_6$–$C_{12}$-cycloalkyl or $C_6$–$C_1$ $C_{10}$- or $C_{14}$-aryl which is unsubstituted or substituted by one or more $C_1$–$C_4$-alkyl groups which may be interrupted by —NH— or —$N(R^6)$—, one or more $C_1$–$C_4$-alkoxy, $C_1$–$C_4$-alkylthio and/or OH groups, one or more —$NO_2$, —$CF_3$ and/or —CN, hydroxyethoxy, phenoxy, ureido, carbamoyl, sulfamoyl, benzeneazo, tolueneazo, anilinocarbonyl, anilinosulfonyl, —S—$CH_2$—CH(OH)—$CH_2$—S—R and/or one or two —$N(R^7)(R^8)$, $R^7$ and $R^8$ being as defined above and $R^8$ additionally also being acetyl or methoxyphenyl, or in which $R^5$ is anthraquinonyl, hydroxyanthraquinonyl, $C_1$–$C_{10}$-heteroaryl which is unsubstituted or substituted by —OH, phenyl or $C_1$–$C_4$-alkyl, or $C_7$–$C_{14}$-aralkyl which is unsubstituted or substituted by —OH, one or more $C_1$–$C_4$-alkoxy groups or by —$N(R^6)_2$, $R^6$ being as defined above, or $R^5$ is —$CH_2$—CH(OH)$CH_2$—S—R or $R^5$ is a divalent $C_2$–$C_{12}$-aliphatic radical which is derived from a $C_2$–$C_{12}$-alkane disubstituted by —$NH_2$ and can be unsubstituted or substituted by —OH, —$OCH_3$ or —$N(R^6)_2$, $R^6$ being as defined above, and may be interrupted by —O—, —S— or —$N(R^9)$—, $R^9$ being unsubstituted or OH-substituted $C_1$–$C_4$-alkyl or —$CH_2$—CH(OH)—$CH_2$—S—R, or $R^5$ is a divalent to tetravalent $C_6$–$C_{12}$-cycloaliphatic radical which is derived from a $C_6$–$C_{12}$ cycloalkane disubstituted or tetrasubstituted by —$NH_2$ and can be unsubstituted or substituted by $C_1$–$C_4$-alkyl, or $R^5$ is a radical of the formula

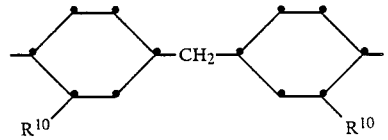

in which $R^{10}$ is hydrogen or $C_1$–$C_4$-alkyl, or $R^5$ is a radical of the formula:

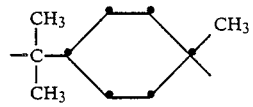

or a divalent or trivalent $C_6$-, $C_{10}$- or $C_{14}$-aromatic radical which is derived from a $C_6$-, $C_{10}$- or $C_{14}$-aromatic disubstituted or trisubstituted by —$NH_2$ and can be unsubstituted or substituted by —OH, —$NO_2$ or $C_1$–$C_4$-alkyl, or $R^5$ is anthraquinonylene, 2,3-dihydroanthraquinonylene or a radical of the formula

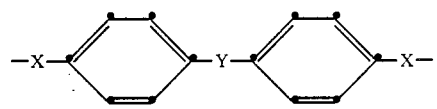

in which X is —$CH_2$— or a direct bond and Y is —$CH_2$—, —$C(C_6H_5)H$—, —S—S—, —NH— or a direct bond, or $R^5$ is a divalent or trivalent $C_2$–$C_{10}$-heteroaromatic radical which is derived from a $C_2$–$C_{10}$-heteroaromatic ring disubstituted or trisubstituted by —$NH_2$ and is unsubstituted or substituted by —OH or $C_6$- or $C_{10}$-aryl, or $R^5$ is a divalent $C_7$–$C_{14}$-araliphatic radical which is derived from a $C_7$–$C_{14}$-aralkane disubstituted by —$NH_2$, or $R^4$ and $R^5$ together with the N atom to which they are linked form a $C_1$–$C_7$-azacyclic ring which can be aromatic or non-aromatic and may contain one or more N, O or S atoms, the N atom being unsubstituted or substituted by $C_1$–$C_4$-alkyl which in turn can be substituted by —OH, and the $C_1$–$C_7$-azacyclic ring can be unsubstituted or substituted on one C atom by $C_1$–$C_4$-alkyl, =O or =S, or $R^4$ and $R^5$ together with the N atom to which they are linked are 2,2,4-trimethyl-1,2-dihydroquinolyl, a part of a $C_1$–$C_7$-azacyclic divalent to hexavalent ring or a radical of the formulae

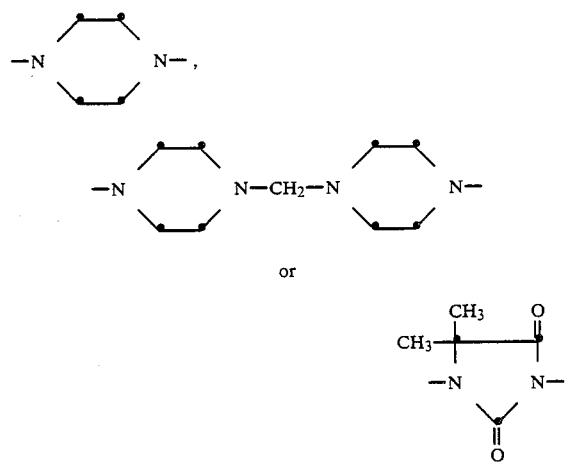

or

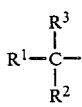

A special embodiment comprises compounds of the formula Ia, wherein n is 1.

A further embodiment comprises compounds of the formula Ia, wherein n is 2 to 6, but preferably 2.

Compounds of the formula Ia are also preferred, wherein $R^4$ in the formula Ia is hydrogen, $C_6$-, $C_{10}$- or $C_{14}$-aryl which is unsubstituted or substituted by one or two $C_1$-$C_4$-alkyl or —$CF_3$, one or two OH groups or one or two —N($R^7$)($R^8$) and $R^7$ is hydrogen or $C_1$-$C_4$-alkyl and $R^8$ is $C_1$-$C_4$-alkyl or $C_6$- or $C_{10}$-aryl or wherein $R^4$ is anthraquinonyl or is $C_1$-$C_6$-heteroaryl which is unsubstituted or substituted by —OH or $C_1$-$C_4$-alkyl, and $R^5$ is $C_6$-, $C_{10}$- or $C_{14}$-aryl which is unsubstituted or substituted by one or more $C_1$-$C_4$-alkyl groups which may be interrupted by —NH— or —N($R^6$)—, one or more $C_1$-$C_4$-alkoxy, $C_1$-$C_4$-alkylthio and/or OH groups, one or more —$NO_2$, —$CF_3$ and/or —CN, hydroxethoxy, phenoxy, ureido, carbamoyl, sulfamoyl, benzeneazo, tolueneazo, anilinocarbonyl, anilinosulfonyl, —S—$CH_2$—CH(OH)—$CH_2$—S— and/or one or two —N($R^7$)($R^8$), $R^7$ and $R^8$ being as defined above and $R^8$ also being acetyl or methoxyphenyl, or wherein $R^5$ is anthraquinonyl, hydroxyanthraquinonyl or is $C_1$-$C_{10}$-heteroaryl which is unsubstituted or substituted by —OH, phenyl and/or $C_1$-$C_4$-alkyl or $R^5$ is divalent or trivalent $C_6$-, $C_{10}$- or $C_{14}$-aromatic radical which is derived from a $C_6$-, $C_{10}$- or $C_{14}$-aromatic disubstituted or trisubstituted by —$NH_2$ and can be unsubstituted or substituted by —OH, —$NO_2$ or $C_1$-$C_4$-alkyl, or $R^5$ is anthraquinonylene, 2,3-dihydroanthraquinoylene or a radical of the formula

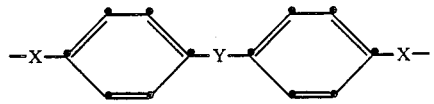

in which X is a direct bond and Y is —$CH_2$—, —C($C_6H_5$)H—, —S—S—, —NH— or a direct bond, or $R^5$ is a divalent or trivalent $C_2$-$C_{10}$ heteroaromatic radical which is derived from a $C_2$-$C_{10}$-heteroaromatic disubstituted or trisubstituted by —$NH_2$ and is unsubstituted or substituted by —OH or $C_6$- or $C_{10}$-aryl, or $R^4$ and $R^5$ together with the N atom to which they are linked form a $C_1$-$C_7$-azacyclic ring which is aromatic and may contain one or more N, O or S atoms, or $R^4$ and $R^5$ together with the N atom to which they are linked are a 2,2,4-trimethyl-1,2-dihydroquinolyl radical.

Compounds of the formula Ia are particularly preferred, wherein R is a radical of the formula $$R^1-\underset{\underset{R^2}{|}}{\overset{\overset{R^3}{|}}{C}}-$$

in which $R^1$, $R^2$ and $R^3$ together with the carbon atom to which they are linked form $C_8$-$C_{12}$-alkyl and none of these substituents $R^1$, $R^2$ and $R^3$ may be hydrogen.

Furthermore, the present invention relates to the compound 1-ethylthio-3-(triazol-3-yl)-amino-propan-2-ol.

Examples of compounds of the formula I are:

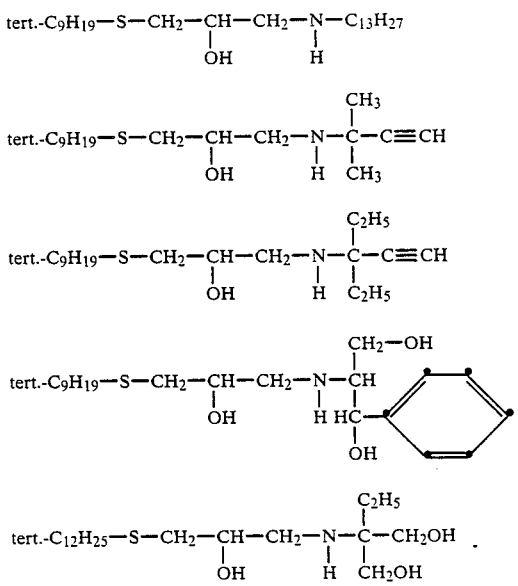

-continued
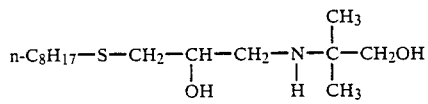
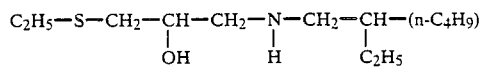
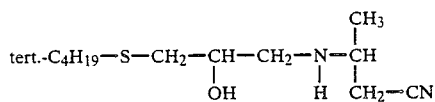
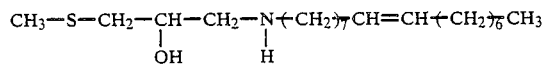
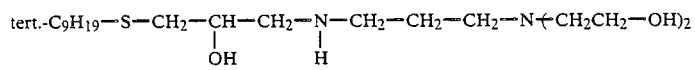
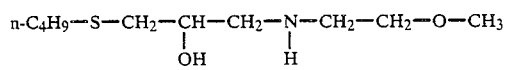
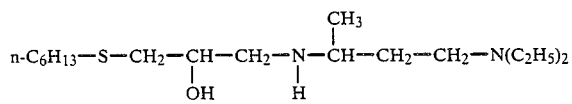
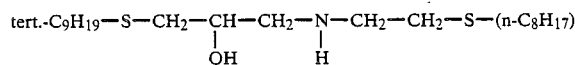
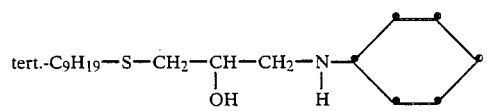
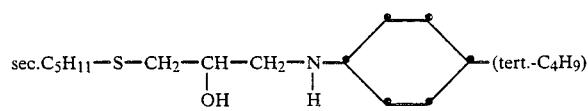
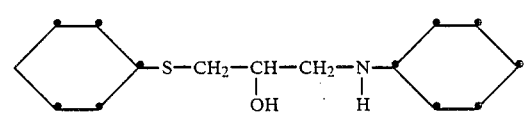
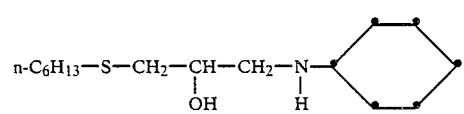
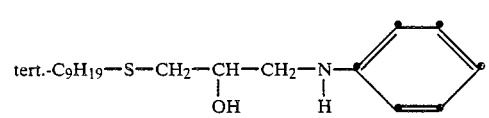
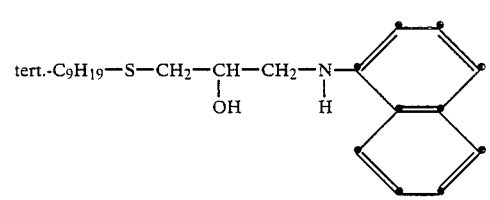

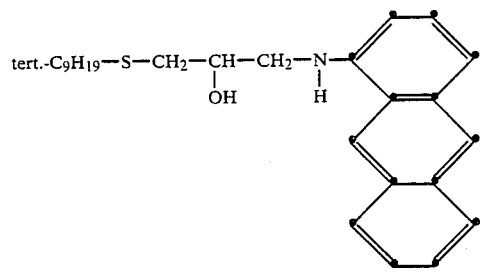
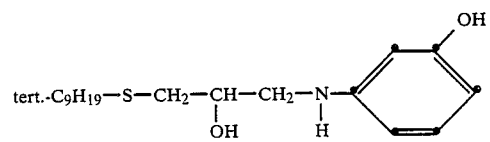
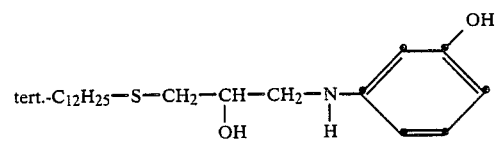
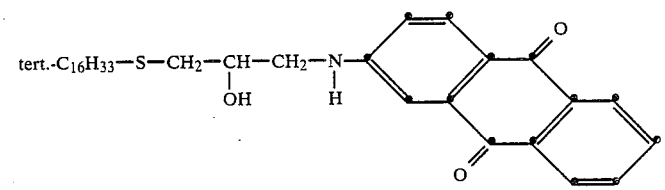
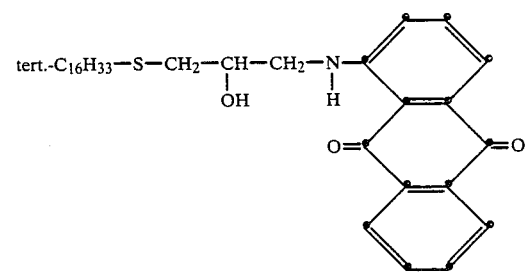
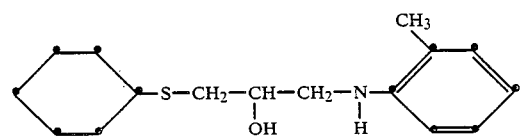
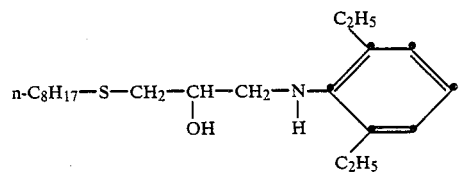
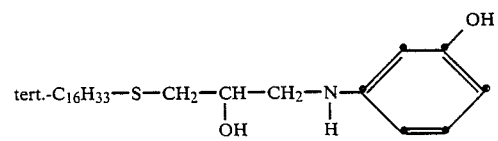
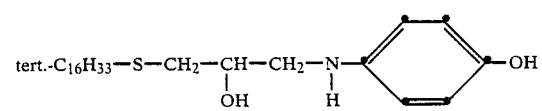

-continued
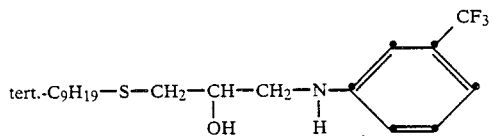
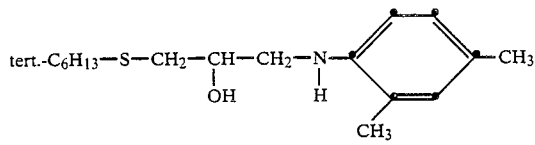
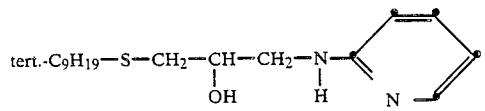
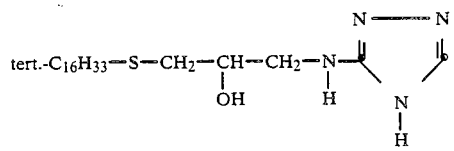
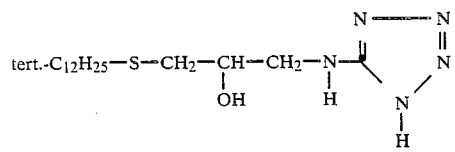
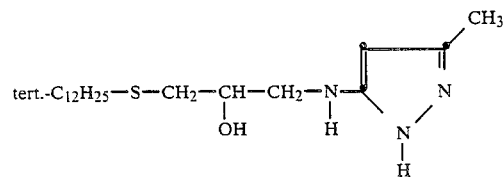
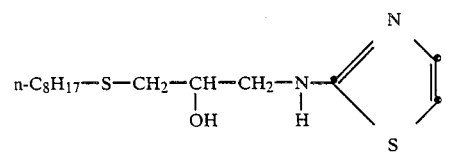
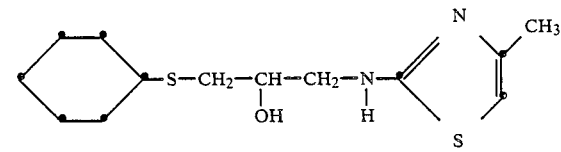
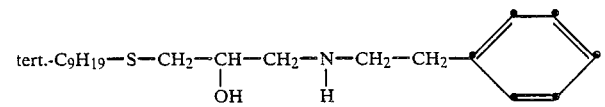
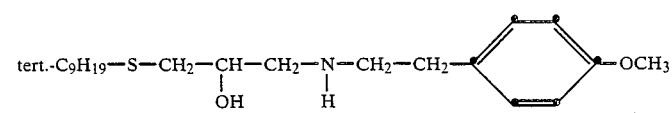
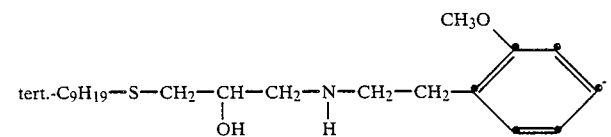

-continued
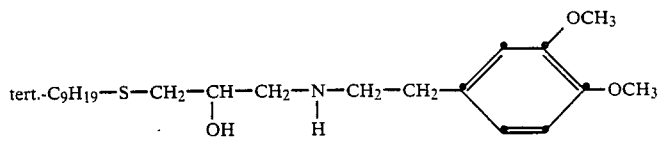
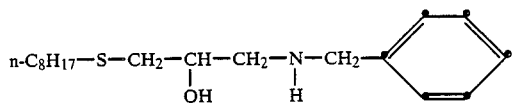
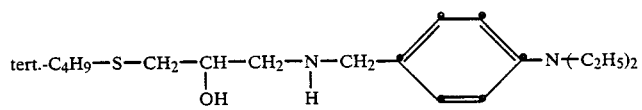
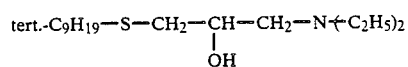
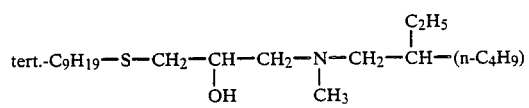
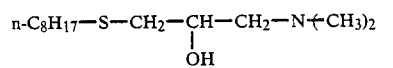
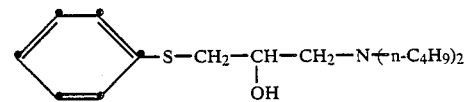
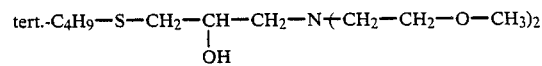
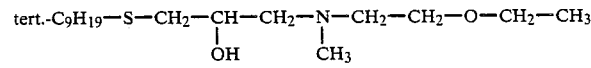
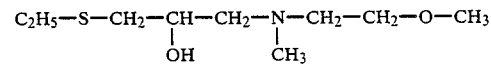
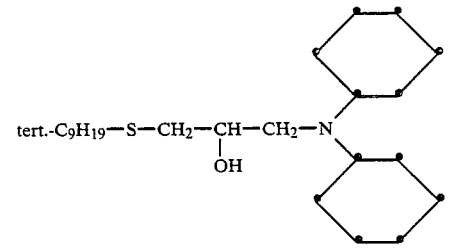
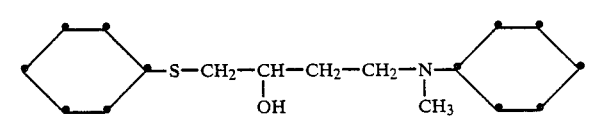
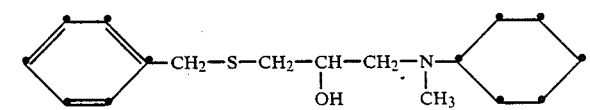

-continued
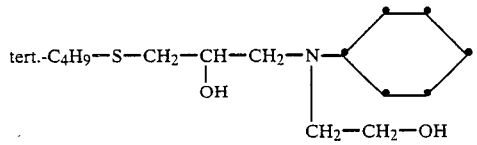
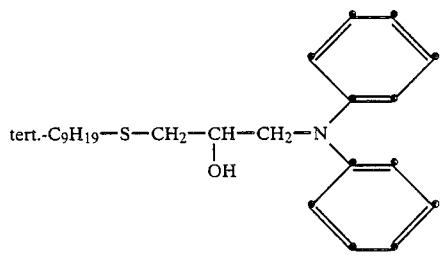
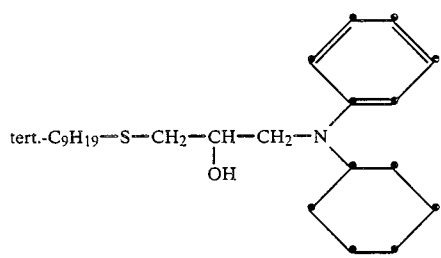
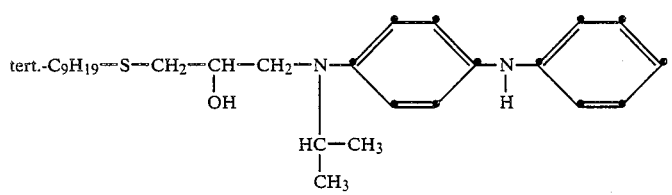
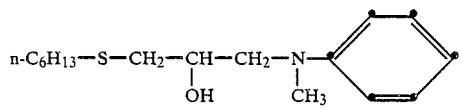
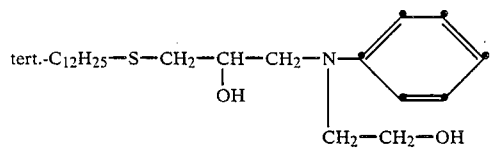
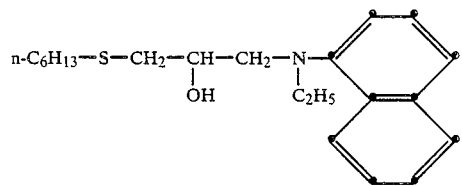
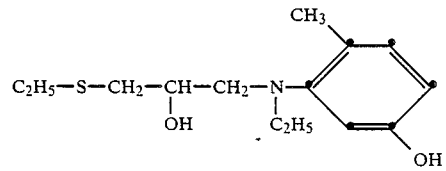

-continued
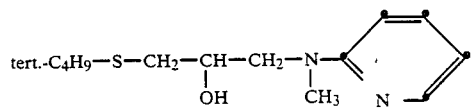
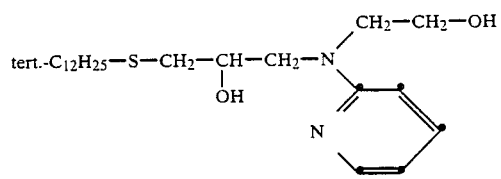
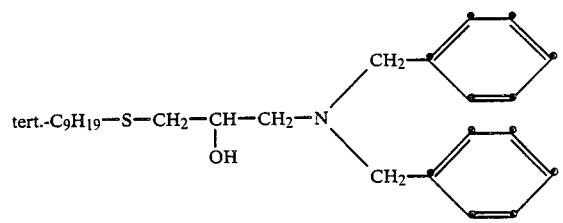
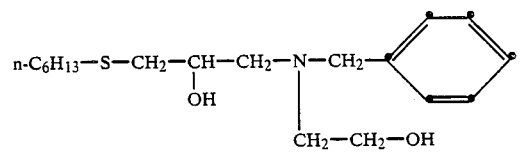
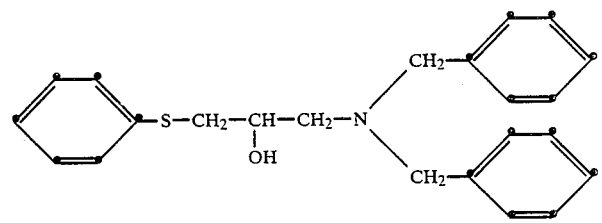
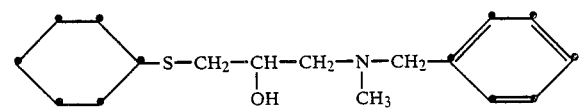
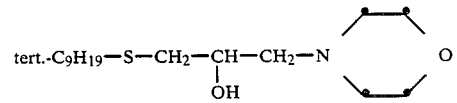
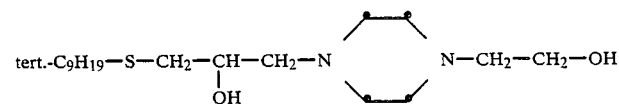
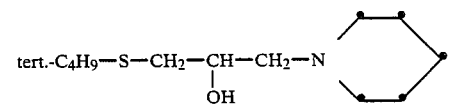
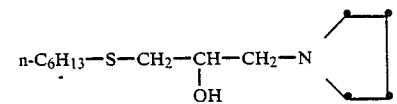

-continued
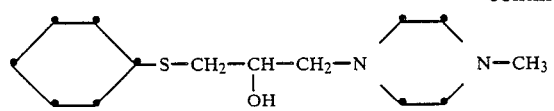
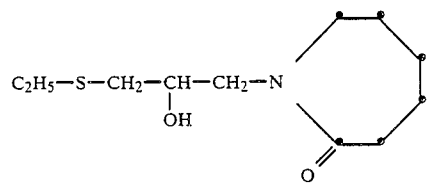
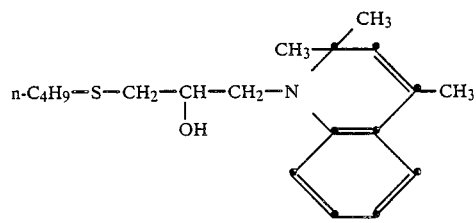
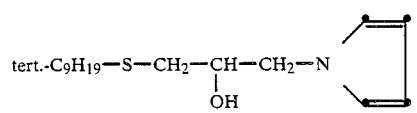
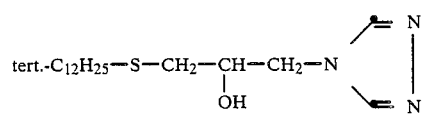
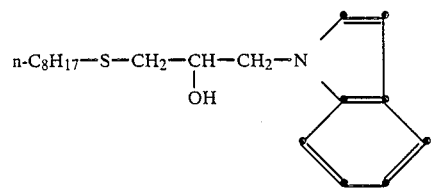
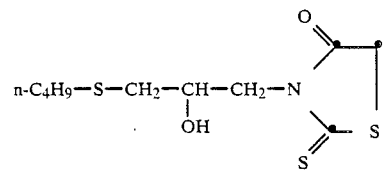
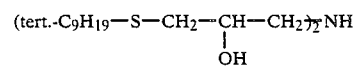
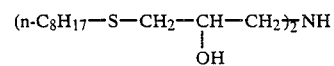
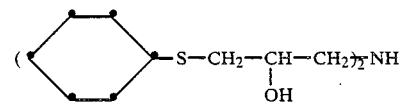
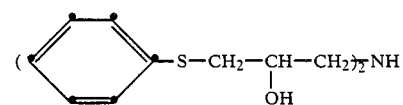
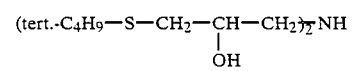

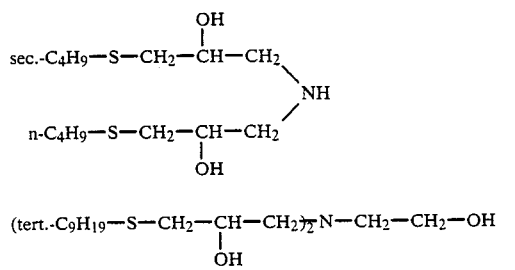
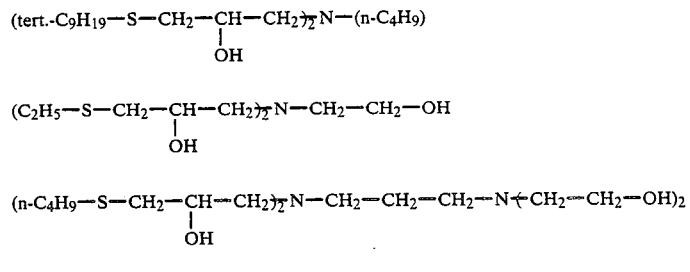
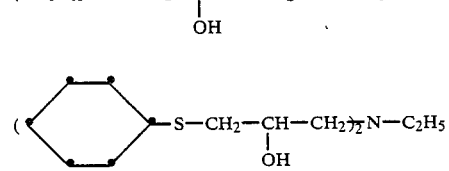
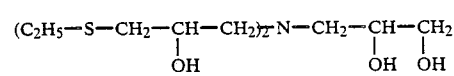
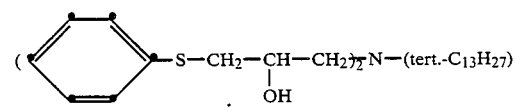
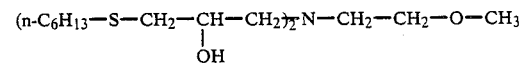
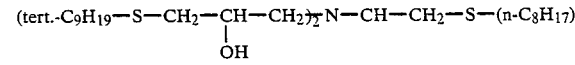
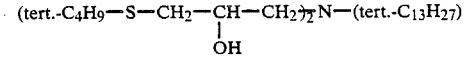
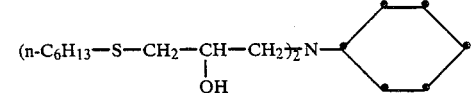
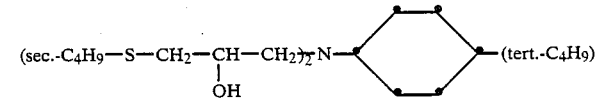
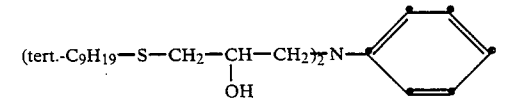

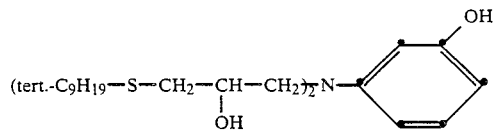
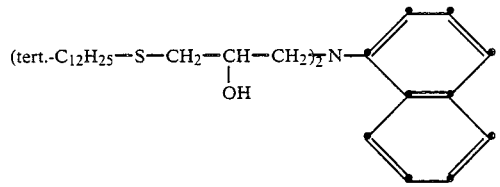
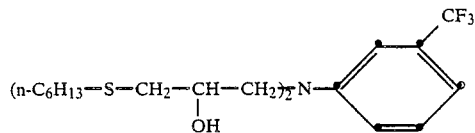
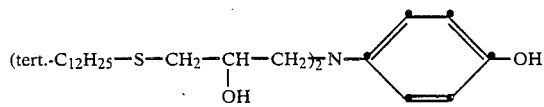
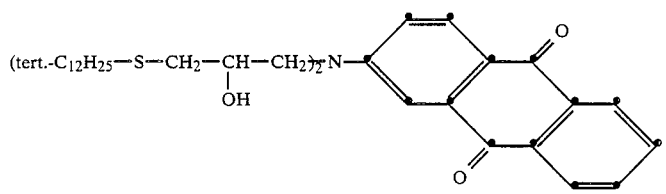
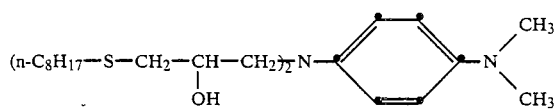
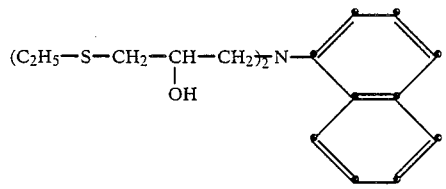
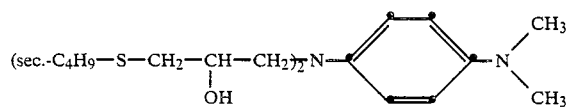
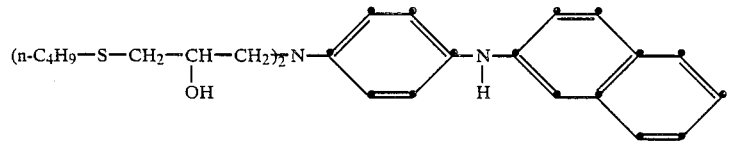
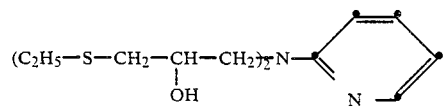

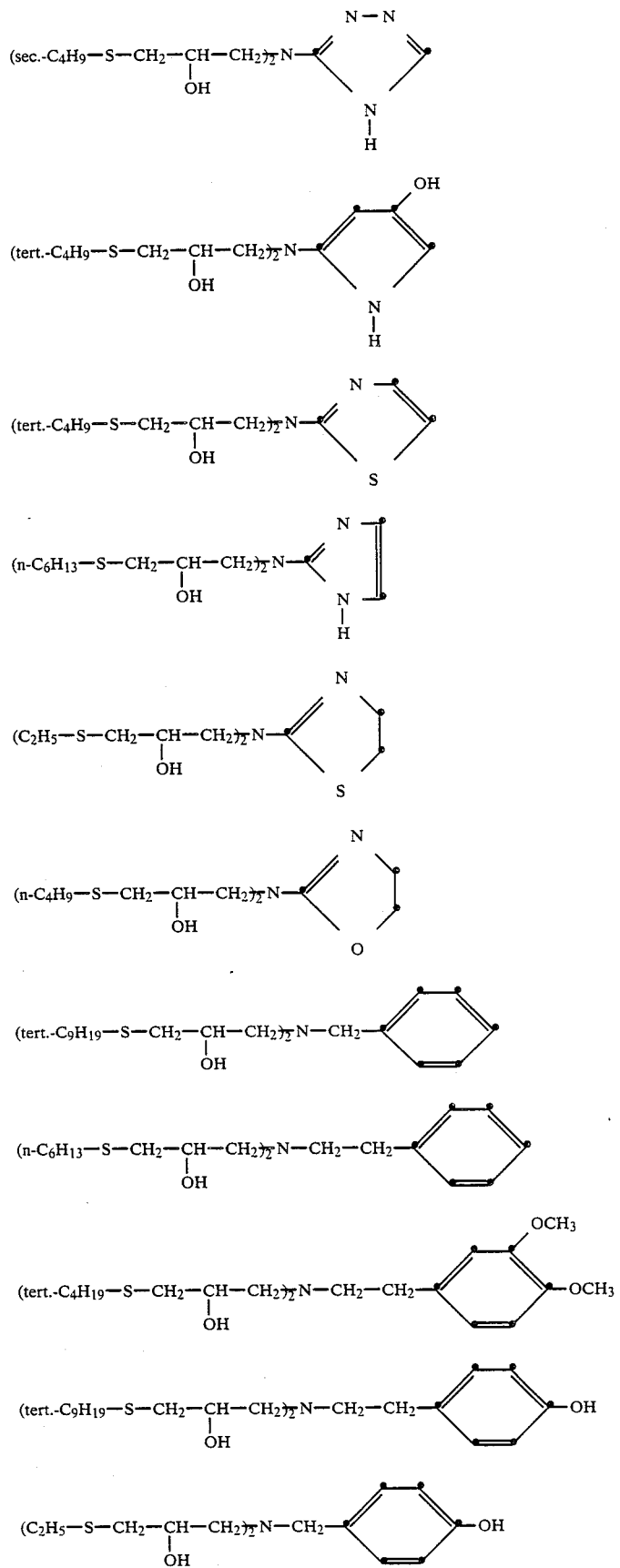

-continued
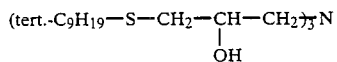
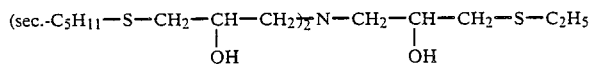
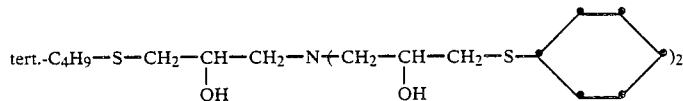
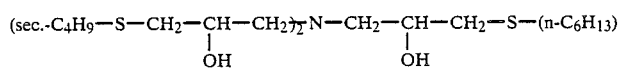
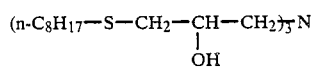
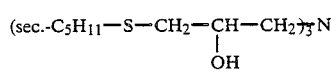
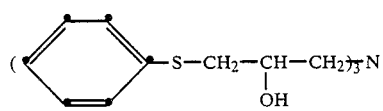
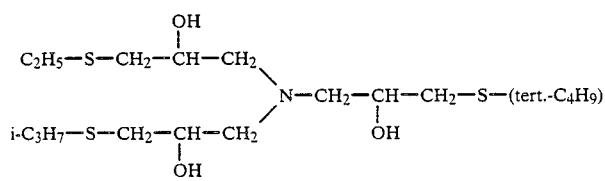
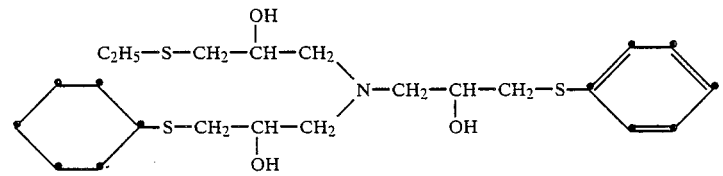
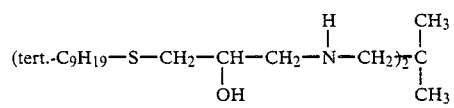
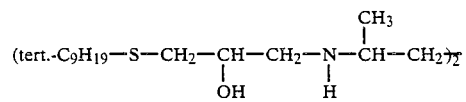
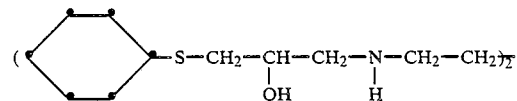
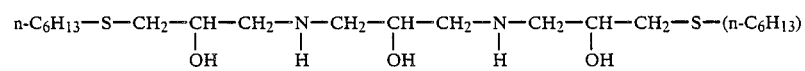
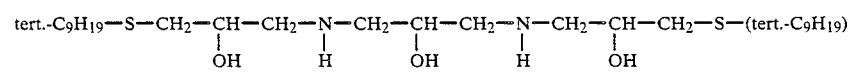
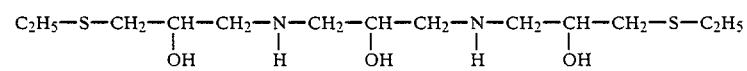

-continued
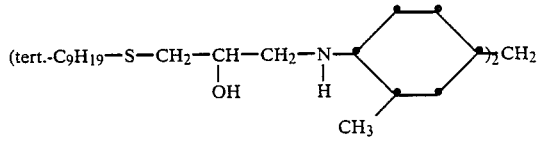
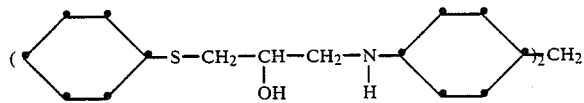
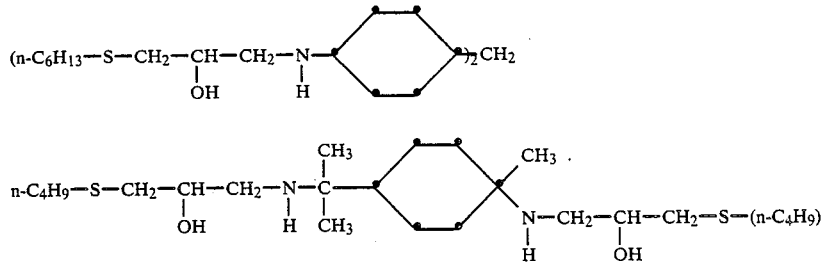
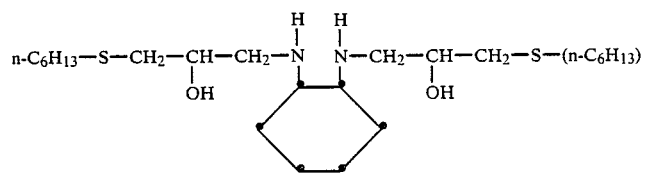
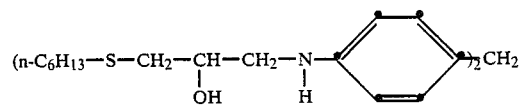
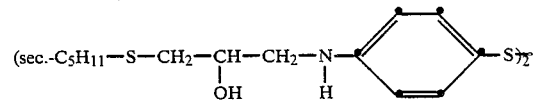
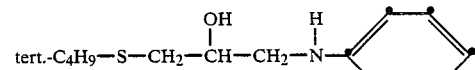
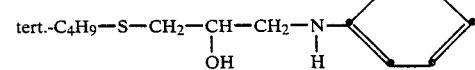
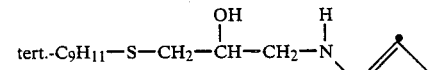
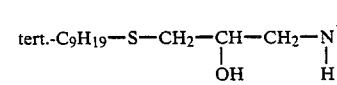
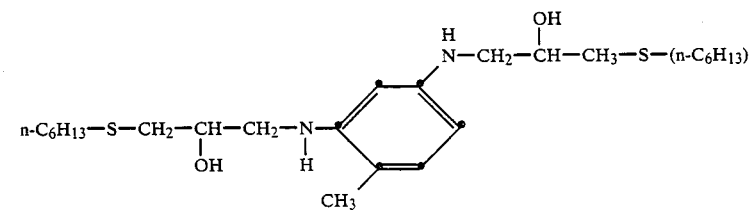

-continued
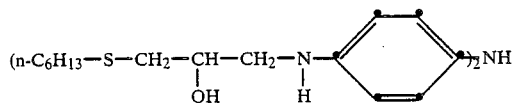
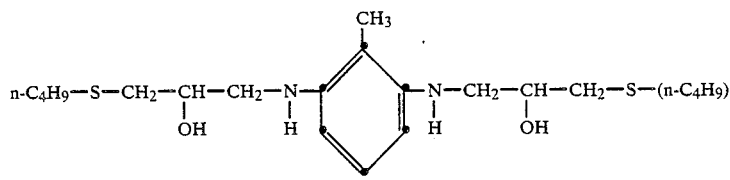
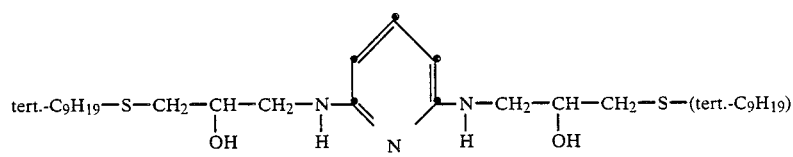
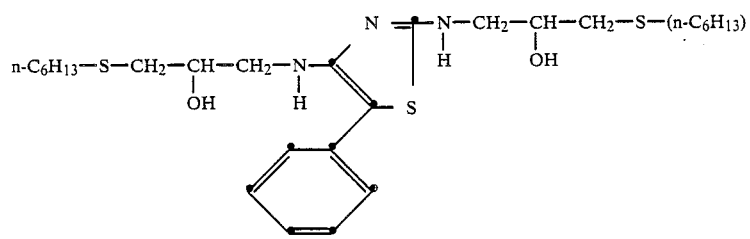
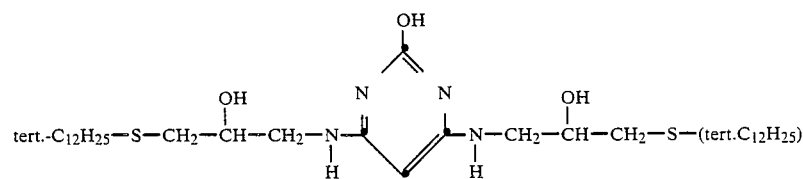
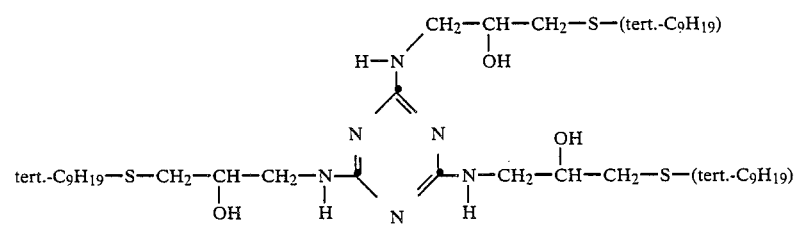
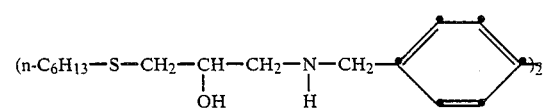
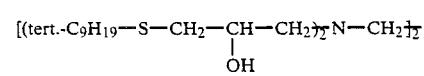

-continued
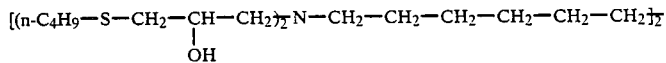
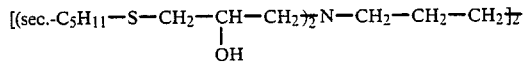
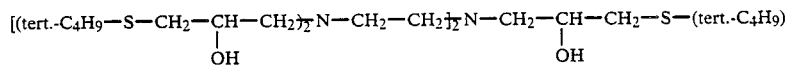
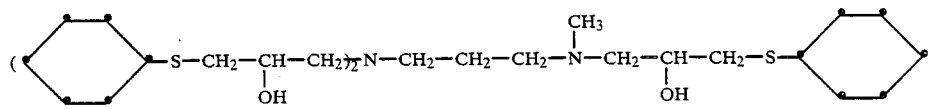
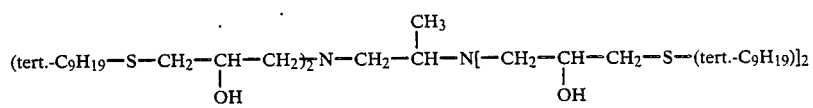
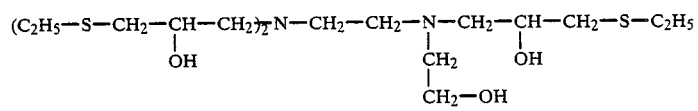
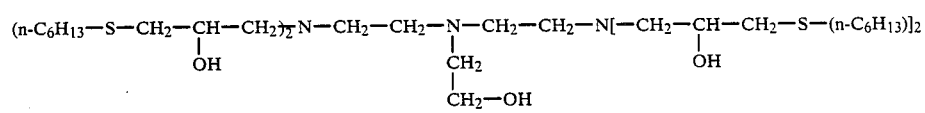
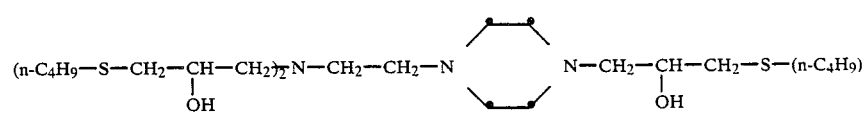
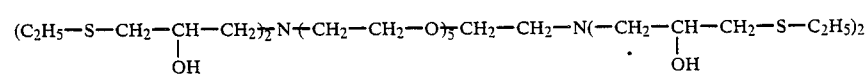
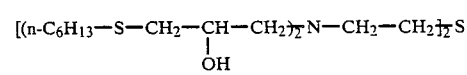
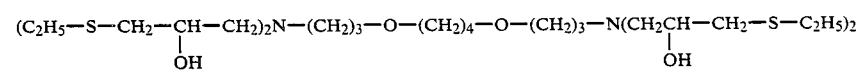
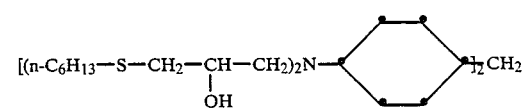
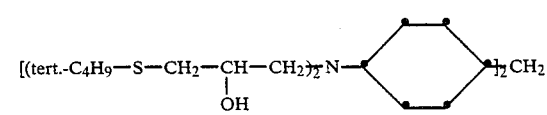
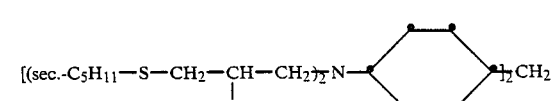

-continued
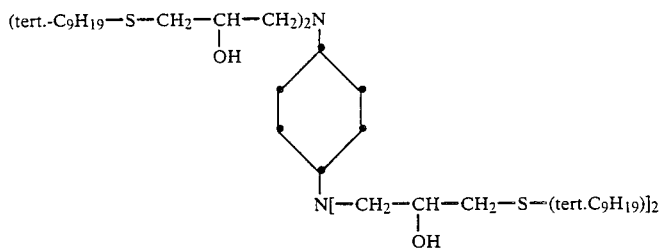
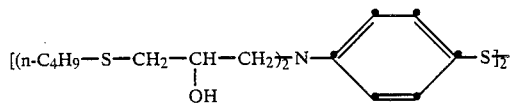
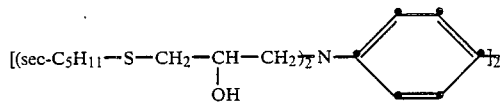
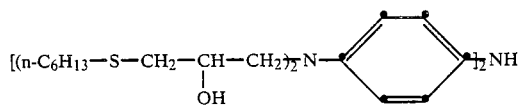
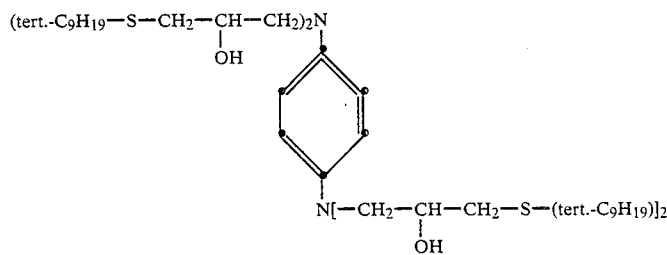
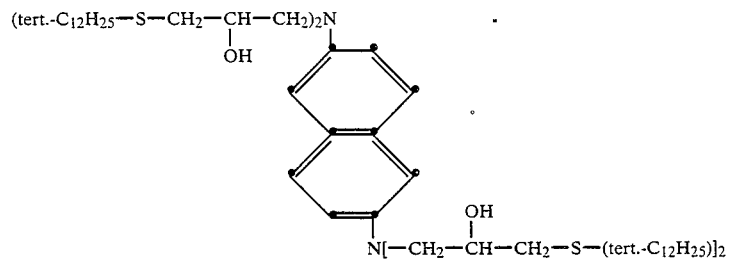
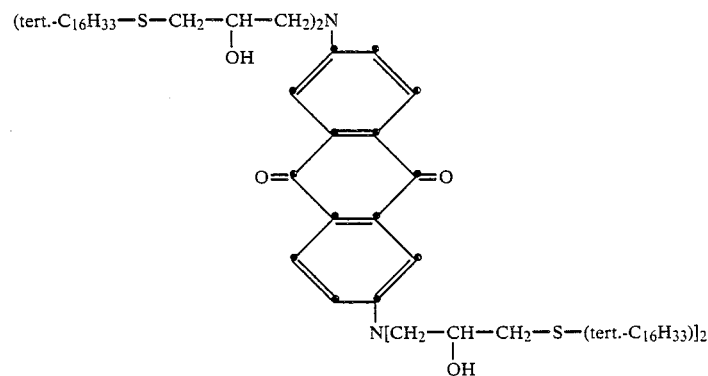

-continued
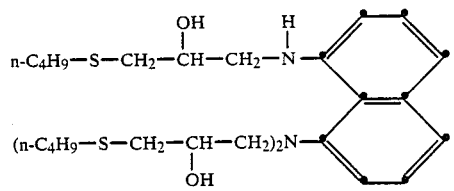
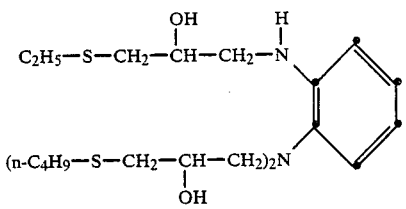
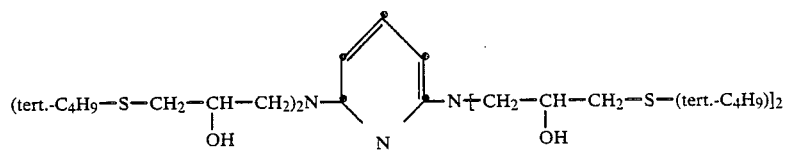
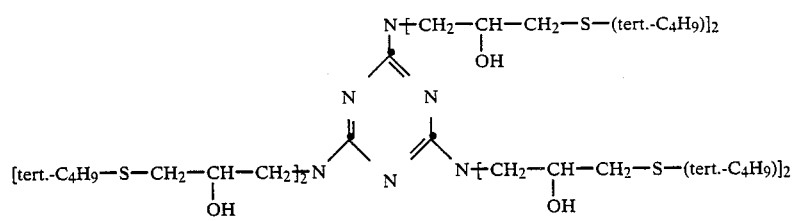
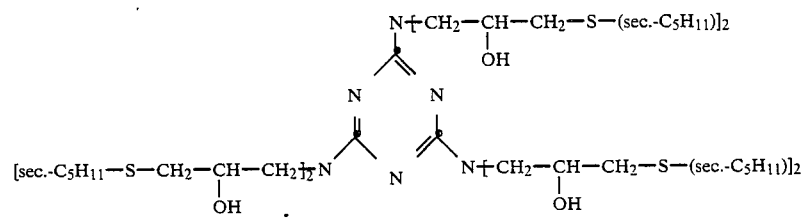
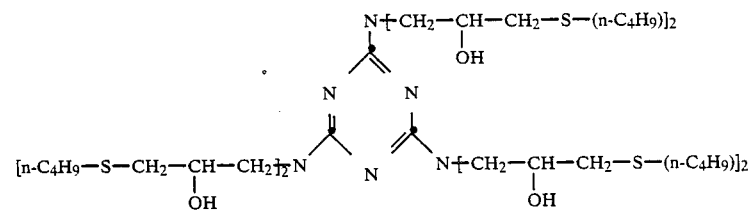
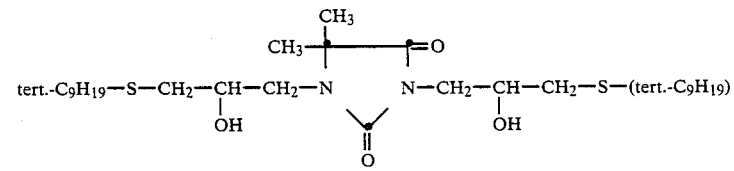
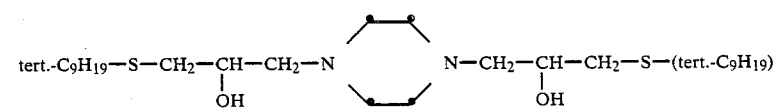
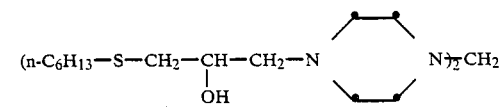

-continued

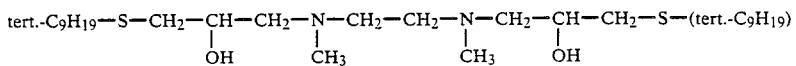

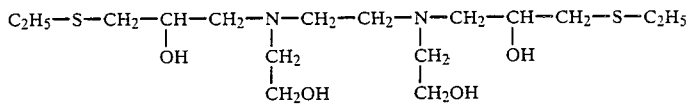

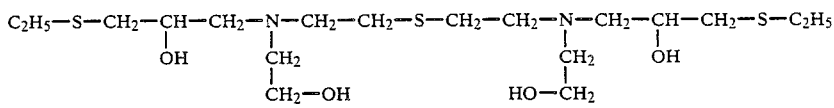

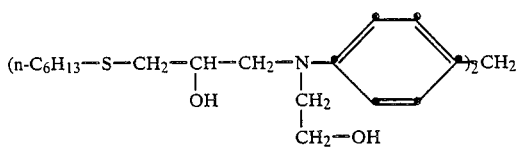

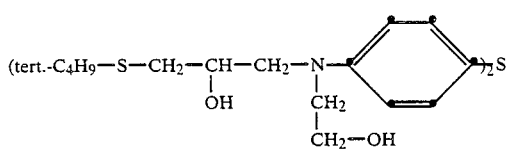

The compounds of the formula I or Ia can advantageously be obtained in a known manner by reacting a glycidyl thioether of the formula II

 (II)

with an amine of the formula III

 (III)

R, $R^4$ and $R^5$ being as defined above.

A solvent can be used for the reaction. It is, however, advantageous to do without a solvent, since the glycidyl thioethers, which are liquid almost without exception, act themselves as a solvent in the case of solid amino compounds.

The reaction temperatures are advantageously between room temperature and a maximum of 150° C., depending on the basicity of the amino compounds.

The compounds of the formula I can, however, also be obtained by reacting a mercaptan of the formula IV

R—SH  (IV)

with a N-glycidyl compound of the formula V

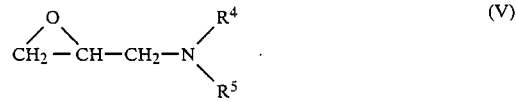 (V)

A further possibility of preparing the compounds of the formula I comprises reacting an amine of the formula III or a mercaptan of the formula IV with chlorohydrin derivatives of the formulae VI and VII, each as are (can be) obtained in the addition of epichlorohydrin to HS or HN compounds (even in situ).

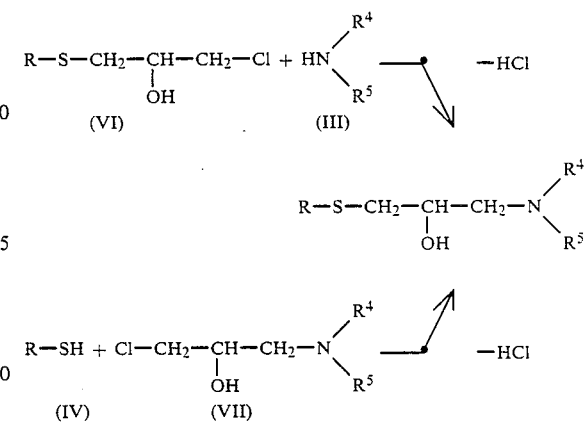

In this case, a hydrogen chloride acceptor in the form of a base is necessary.

In general, the $NH_2$ group reacts bifunctionally, except in the case of steric hindrance, for example in the case of an $NH_2$ group which is bonded to a tertiary carbon atom and reacts only monofunctionally. For the monofunctional conversion of a normal $NH_2$ group, a certain excess of amino compound is required, which excess can later be separated off by distillation or on the basis of different solution properties.

The following are examples of preferred amines of the formula III:

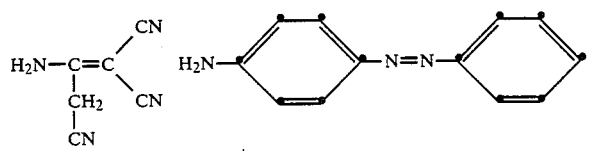
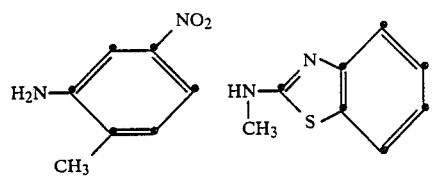
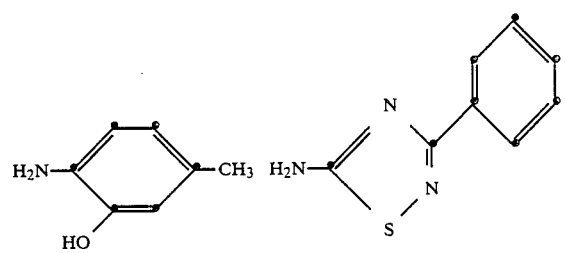
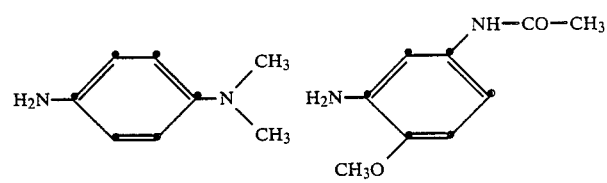
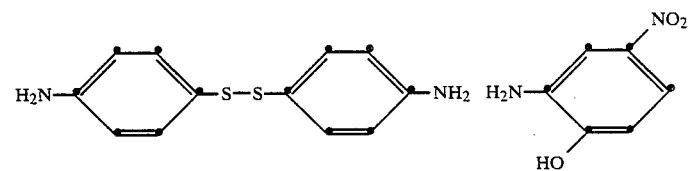
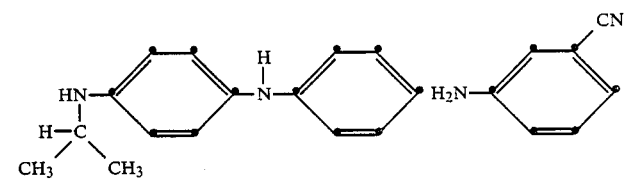
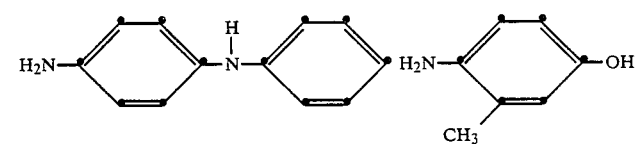
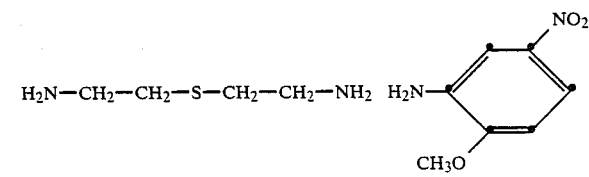

-continued
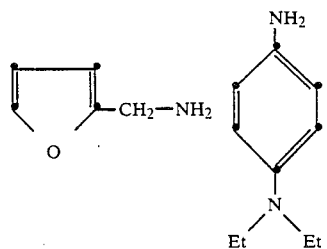
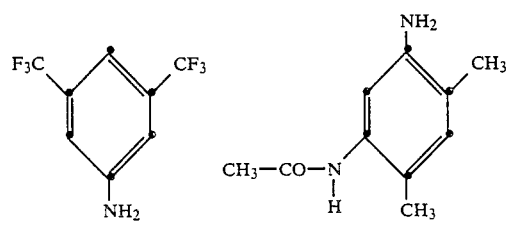
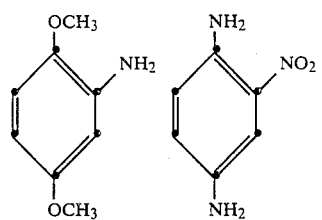
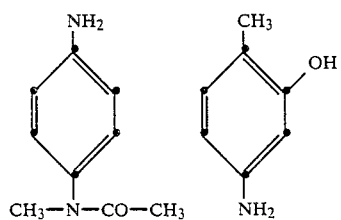
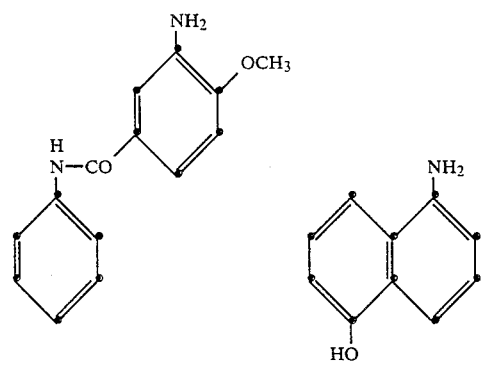
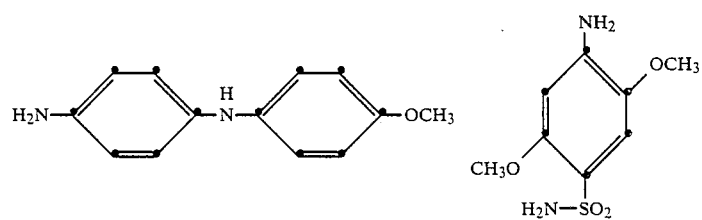

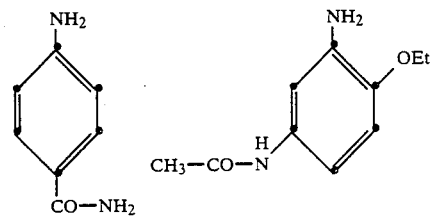
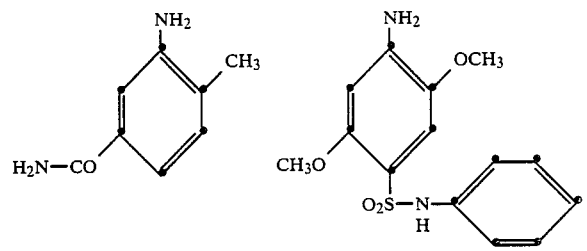
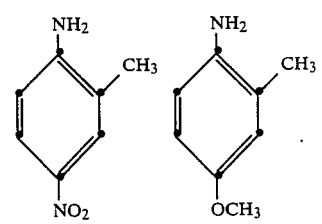
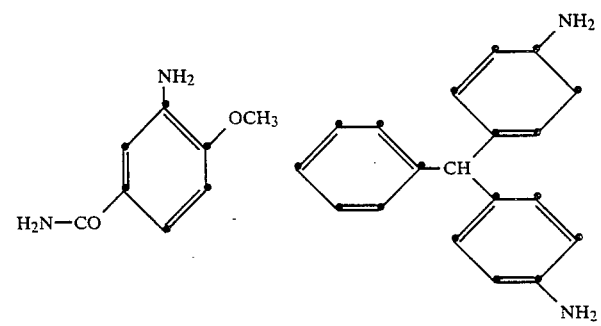
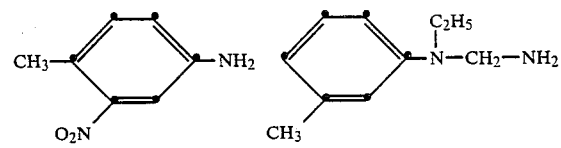
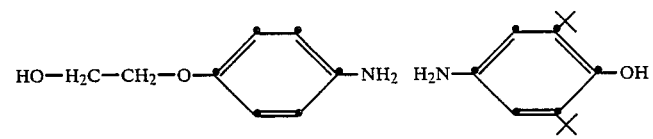
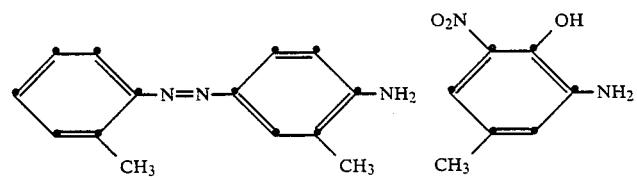

-continued
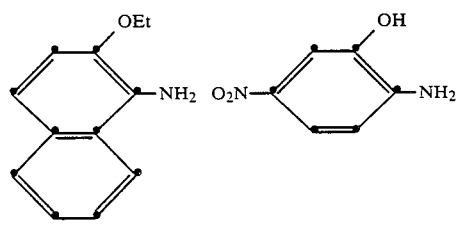
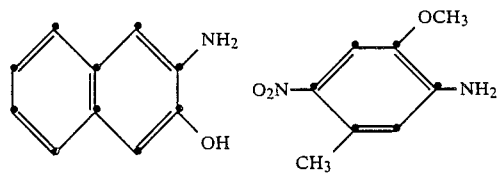
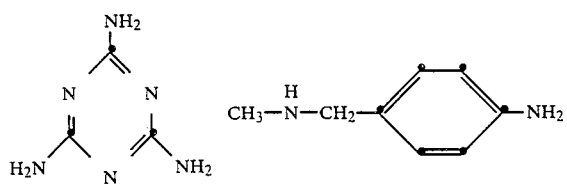
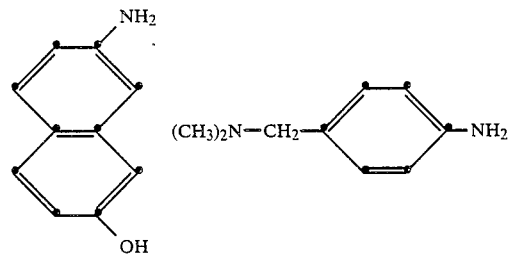
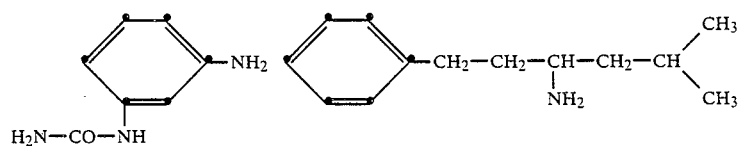
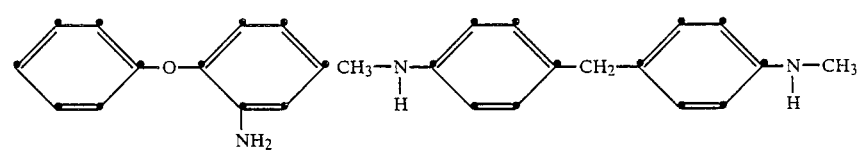
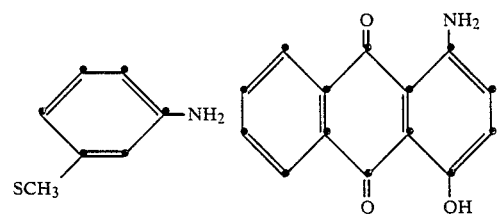
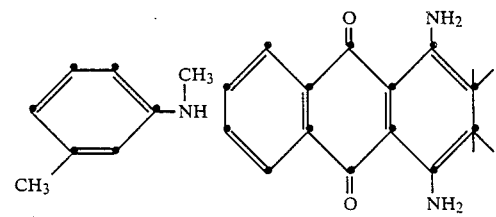

-continued

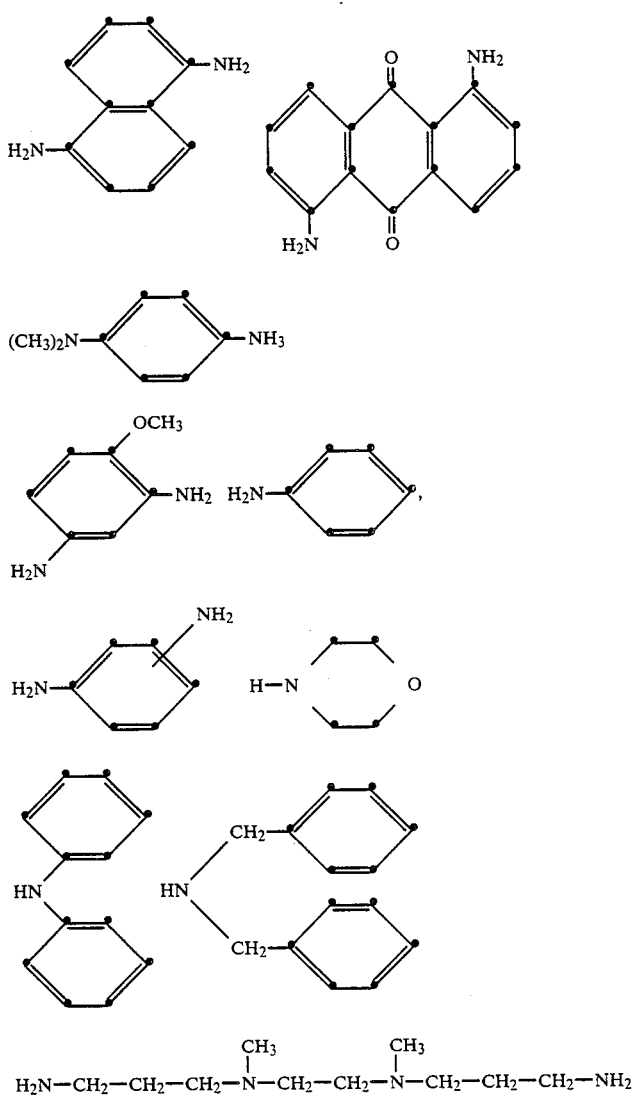

$$H_2N-CH_2-CH_2-CH_2-\underset{\underset{CH_3}{|}}{N}-CH_2-CH_2-\underset{\underset{CH_3}{|}}{N}-CH_2-CH_2-CH_2-NH_2$$

The invention also relates to the use of compounds of the formulae I or Ia as additives in lubricants, hydraulic fluids or metal-working fluids.

The compounds of the formula I or Ia are in general of a liquid nature, but have different viscosities. Adequate quantities of them are soluble in lubricants, hydraulic fluids and metal-working fluids. In the case of the representatives of high viscosity, dilution with, for example, a paraffin oil or an appropriate base oil provides an advantageous made-up form.

The compounds according to the invention are outstandingly suitable as additives for lubricants, hydraulic fluids and metal-working fluids, in particular for lubricants and hydraulic fluids and very particularly for lubricants, and lead to an improvement in the use properties, for example the extreme-pressure and anti-wear properties.

The compounds of the formula I are added to the lubricants, hydraulic fluids and metal-working fluids advantageously in a quantity of 0.01 to 10% by weight, preferably in a quantity of 0.05 to 5% by weight, relative to the lubricant, the hydraulic fluid or the metal-working fluid.

Such lubricant, hydraulic and metal-working systems can be of a polar or non-polar nature. The selection criteria result from the solubility properties of the corresponding compounds.

Those skilled in the art are familiar with the relevant lubricants, hydraulic fluids or metal-working fluids, and these are described, for example, in "Schmiermittel Taschenbuch [Lubricants Pocketbook]" (Hüthig Verlag, Heidelberg, 1974) or in "Ullmanns Encyclopädie der technischen Chemie [Ullmann's Encyclopaedia of Industrial Chemistry]", volume 13, pages 85–94 (Verlag Chemie, Weinheim, 1977) or in D. Klamann "Schmierstoffe und verwandte Produkte [Lubricants and related products]", pages 158–174 (Verlag Chemie, Weinheim, 1982).

Apart from mineral oils, particularly suitable examples are poly-α-olefins, ester-based lubricants, phosphates, glycols, polyglycols and polyalkylene glycols, and their mixtures with water, and water itself.

The lubricants, hydraulic fluids, metal-working fluids can also contain other additives which are added in order to improve the base properties of these substances even further; these include: antioxidants, metal passivators, rust inhibitors, viscosity index improvers, pour point depressants, dispersants, detergents and other extreme-pressure additives and anti-wear additives.

Examples of phenolic antioxidants

1. Alkylated monophenols 2,6-Di-tert-butyl-4-methylphenol, 2,6-di-tert-butylphenol, 2-tert-butyl-4,6-dimethylphenol, 2,6-di-tert-butyl-4-ethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol and o-tert-butylphenol.

2. Alkylated hydroquinones 2,6-Di-tert-butyl-4-methoxyphenol, 2,5-di-tert-butyl-hydroquinone, 2,5-di-tert-amyl-hydroquinone and 2,6-diphenyl-4-octadecyloxyphenol.

3. Hydroxylated thiodiphenyl ethers 2,2'-Thio-bis-(6-tert-butyl-4-methylphenol), 2,2'-thio-bis-(4-octylphenol), 4,4'-thio-bis-(6-tert-butyl-3-methylphenol) and 4,4'-thio-bis-(6-tert-butyl-2-methylphenol).

4. Alkylidene-bisphenols 2,2'-Methylene-bis-(6-tert-butyl-4-methylphenol), 2,2'-methylene-bis-(6-tert-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4-iso-butylphenol), 2,2'-methylene-bis-[6-(α-methylbenzyl)-4-nonylphenol], 2,2'-methylene-bis-]6-(α,α-dimethylbenzyl)-4-nonylphenol], 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)-butane, 2,6-di-(3-tert-butyl-5-methyl-2-hydroxybenzyl)-4-methylphenol, 1,1,3-tris-(5-tert-butyl-4-hydroxy-2-methylphenyl)-3-n-dodecyl-mercaptobutane, ethylene glycol bis-[3,3-bis-(3'-tert-butyl-4'-hydroxyphenyl)-butyrate], di-(3-tert-butyl-4-hydroxy-5-methylphenyl)-dicyclopentadiene and di-[2-(3'-tert-butyl-2'-hydroxy-5'-methylbenzyl)-6-tert-butyl-4-methyl-phenyl]terephthalate.

5. Benzyl compounds 1,3,5-Tri-(3,5-di-tert-butyl-4-hydroxybenzyl)-2,4,6-trimethylbenzene, di-(3,5-di-tert-butyl-4-hydroxybenzyl)sulfide, isooctyl 3,5-di-tert-butyl-4-hydroxybenzyl-mercaptoacetate, bis-(4-tert-butyl-3-hydroxy-2,6-dimethylbenzyl) dithiol-terephthalate, 1,3,5-tris-(3,5-di-tert-butyl-4-hydroxybenzyl)isocyanurate, 1,3,5-tris-(4-tert-butyl-3-hydroxy-2,6-dimethylbenzyl)isocyanurate, dioctadecyl 3,5-di-tert-butyl-4-hydroxybenzyl-phosphonate and the calcium salt of monoethyl 3,5-di-tert-butyl-4-hydroxybenzyl-phosphonate.

6. Acylaminophenols

Lauric acid 4-hydroxy-anilide, stearic acid 4-hydroxy-anilide, 2,4-bis-octylmercapto-6-(3,5-di-tert-butyl-4-hydroxyanilino)-s-triazine and octyl N-(3,5-di-tert-butyl-4-hydroxyphenyl)-carbamate.

7. Esters of β-(3,5-di-tert-butyl-4-hydroxyphenyl)-propionate with monohydric or polyhydric alcohols, for example with methanol, diethylene glycol, octadecanol, triethylene glycol, 1,6-hexanediol, pentaerythritol, neopentyl glycol, tris-hydroxyethyl isocyanurate, thiodiethylene glycol and di-hydroxyethyl-oxalic acid diamide.

8. Esters of β-(5-tert-butyl-4-hydroxy-3-methylphenyl)propionic acid with monohydrici or polyhydric alcohols, for example with methanol, diethylene glycol, octadecanol, triethylene glycol, 1,6-hexanediol, pentaerythritol, neopentyl glycol, tris-hydroxyethyl isocyanurate, thiodiethylene glycol and di-hydroxyethyl-oxalic acid diamide.

9. Amides of β-(3,5-di-tert-butyl-4-hydroxyphenyl)-propionic acid, for example N,N'-di-(3,5-di-tert-butyl-4-hydroxyphenylpropionyl)-hexamethylenediamine, N,N'-di-(3,5-di-tert-butyl-4-hydroxyphenylpropionyl)-trimethylenediamine and N,N'-di-(3,5-di-tert-butyl-4-hydroxyphenylpropionyl)-hydrazine.

Examples of amine-type antioxidants:

N,N'-Di-isopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methylpentyl)-p-phenylenediamine, N,N'-bis(1-methyl-heptyl)-p-phenylenediamine, N,N'-di-(naphthyl-2)-p-phenylenediamine, N-isopropyl-N'-phenyl-p-phenylenediamine, N-(1,3-dimethyl-butyl)-N'-phenyl-p-phenylenediamine, N-(1-methylheptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, diphenylamine, 4-isopropoxy-diphenylamine, N-phenyl-1-naphthylamine, N-phenyl-2-naphthylamine, octylated diphenylamine, 4-n-butylaminophenol, 4-butyrylamino-phenol, 4-nonanoylaminophenol, 4-dodecanoylamino-phenol, 4-octadecanoylamino-phenol, di-(4-methoxy-phenyl)-amine, 2,6-di-tert-butyl-4-dimethylamino-methyl-phenyl, 2,4'-diamino-diphenylmethane, 4,4'-diamino-diphenylmethane, N,N,N',N'-tetramethyl-4,4'-diaminodiphenylmethane, 1,2-di-[(2-methyl-phenyl)-amino]-ethane, 1,2-di-(phenylamino)-propane, (o-tolyl)-biguanide, di-[4-(1',3'-dimethy-butyl)-phenyl]-amine, tert-octylated N-phenyl-1-naphthylamine and a mixture of monoalkylated and dialkylated tert-butyl-/tert-octyl-diphenylamines.

Examples of metal passivators are:

for copper, for example triazole, benzotriazole and derivatives thereof, 2-mercaptobenzothiazole, 2,5-dimercaptothiadiazole, salicylidene-propylenediamine and salts of salicyclaminoguanidine.

Examples of rust inhibitors are:

(a) organic acids, their esters, metal salts and anhydrides, for example: N-oleoyl-sarcosine, sorbitan mono-oleate, lead naphthenate, dodecenylsuccinic anhydride, alkenylsuccinic acid half-esters and 4-nonylphenoxyacetic acid.

(b) Nitrogen-containing compounds, for example:

I. primary, secondary or tertiary aliphatic or cycloaliphatic amines and amine salts of organic and inorganic acids, for example oil-soluble alkylammonium carboxylates.

II. Heterocyclic compounds, for example: substituted imidazolines and oxazolines (c) Phosphorus-containing compounds, for example: amine salts of phosphoric acid partial esters.

(d) Sulfur-containing compounds, for example: barium dinonylnaphthalenesulfonates and calcium petroleum-sulfonates.

Examples of viscosity index improvers are:

polymethacrylates, vinylpyrrolidone/methacrylate copolymers, polybutenes, olefin copolymers and styrene/acrylate copolymers.

Examples of pour point depressants are:

polymethacrylates and alkylated naphthalene derivatives.

Examples of dispersants/surfactants are:

polybutenylsuccinimides, polybutenylphosphonic acid derivatives and basic magnesium, calcium and barium sulfonates and phenolates.

Examples of anti-wear additives are:

compounds containing sulfur and/or phosphorus and/or halogen, such as sulfurized vegetable oils, zinc dialkyldithiophosphates, tritolyl phosphate, chlorinated paraffins, and alkyl and aryl disulfides.

EXAMPLE 1

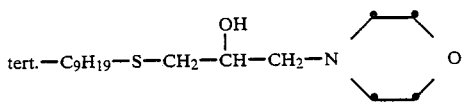

17.4 g of morpholine are introduced into a flask and heated to 90° C., and 47.6 g of tert-nonyl glycidyl thioether are added dropwise with stirring. After the end of the addition, the mixture is stirred for a further 0.5 hour at 90° C. The yield is 100% of theory of a yellow, slightly viscous liquid having a refractive index of $n_D^{20}$: 1.4914.

EXAMPLE 2

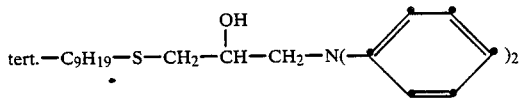

A mixture of 15.2 g of tert-nonylmercaptan and catalytic quantities of sodium hydride is heated to 100° C., and 22.5 g of N-glycidyldiphenylamine (CA 64, 3385 d) are added dropwise with stirring at the same temperature. To complete the reaction, stirring is continued for 1.5 hours at 100° C.

Yield: 37.7 g of a yellow viscous liquid having a refractive index of $n_D^{20}$: 1.5699.

EXAMPLE 3

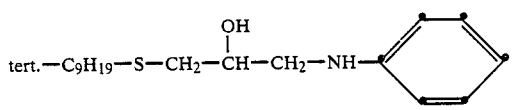

A mixture of 43.3 g of tert-nonyl glycidyl thioether and 46.5 g of aniline is heated for 8 hours with stirring at 100° C. The excess aniline is then distilled off in a water pump vacuum and the residue is fractionated in an oil pump vacuum. This gives 51.1 g ≙ 82.6% of theory of a liquid having a boiling point of 169° C. at 0.08 mbar and a refractive index of $n_D^{20}$: 1.5419.

EXAMPLE 4

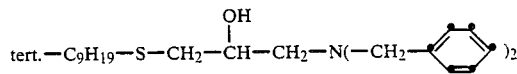

35.7 g of tert-nonyl glycidyl thioether and 14.8 g of dibenzylamine are heated for 15 hours at 100° C. After the reaction has ended, the yield is 100% of theory of a yellow liquid having a refractive index of $n_D^{20}$: 1.5169.

Analogously to Examples 1-4, further compounds are prepared which are compiled in Table 1 which follows.

TABLE 1

| Example No. | Formula | Notes | Boiling point (°C.) | $n_D^{20}$ |
|---|---|---|---|---|
| 5 | tert.-C9H19—S—CH2—CH(OH)—CH2—N(CH2—CH2—OH)(C6H5) | yellow viscous liquuid | | 1.5416 |
| 6 | tert.-C9H19—S—CH2—CH(OH)—CH2—NH—(pyridyl) | | | 1.5445 |
| 7 | tert.-C9H19—S—CH2—CH(OH)—CH2—N(CH3)(C6H5) | | | 1.5383 |

TABLE 1-continued

| Example No. | Formula | Notes | Boiling point (°C.) | $n_D^{20}$ |
|---|---|---|---|---|
| 8 | tert.-C₉H₁₉—S—CH₂—CH(OH)—CH₂—N(H)—CH₂—CH₂—C₆H₅ | colourless liquid | 186–88/ 0.09 mbar | 1.5245 |
| 9 | tert.-C₉H₁₉—S—CH₂—CH(OH)—CH₂—N(H)—CH₂—CH₂—C₆H₃(OCH₃)₂ | viscous liquid | 200–05/ 0.001 mbar | 1.5308 |
| 10 | tert.-C₉H₁₉—S—CH₂—CH(OH)—CH₂—N(H)—CH₂—CH₂—C₆H₄(OCH₃) | yellowish viscous liquid | 176–80/ 0.001 mbar | 1.5278 |
| 11 | tert.-C₉H₁₉—S—CH₂—CH(OH)—CH₂—N(H)—CH₂—CH₂—C₆H₄—OCH₃ | | 185–90/ 0.001 mbar | 1.5269 |
| 12 | tert.-C₉H₁₉—S—CH₂—CH(OH)—CH₂—N(C₆H₅)₂ | | | 1.5326 |
| 13 | tert.-C₉H₁₉—S—CH₂—CH(OH)—CH₂—N—(C₆H₁₁)₂ | | | 1.4956 |
| 14 | (tert.-C₉H₁₉—S—CH₂—CH(OH)—CH—)₂N—C₆H₅ | | | |
| 15 | tert.-C₉H₁₉—S—CH₂—CH(OH)—CH₂—N(H)—naphthyl | | 225–30/ 0.001 mbar | 1.5874 |
| 16 | tert.-C₉H₁₉—S—CH₂—CH(OH)—CH₂—N(H)—anthryl | NMR spectrum | | |

TABLE 1-continued

| Example No. | Formula | Notes | Boiling point (°C.) | $n_D^{20}$ |
|---|---|---|---|---|
| 17 | tert.-$C_9H_{19}$—S—$CH_2$—CH—$CH_2$—N—C—C≡CH, with OH on CH, H on N, and $CH_3$, $CH_3$ on C | | 125–30/0.05 mbar | 1.4900 |
| 18 | (tert.-$C_9H_{19}$—S—$CH_2$—CH(OH)—$CH_2$—)$_2$NH | | | 1.5074 |
| 19 | (tert.-$C_9H_{19}$—S—$CH_2$—CH(OH)—$CH_2$—)$_3$N | | | 1.5046 |
| 20 | [(tert.-$C_9H_{19}$—S—$CH_2$—CH(OH)—$CH_2$—)$_2$N—$CH_2$]$_2$ | | | 1.5075 |
| 21 | tert.-$C_{12}H_{25}$—S—$CH_2$—CH(OH)—$CH_2$—NH—(i-$C_{13}H_{27}$) | | | 1.4645 |
| 22 | tert.-$C_9H_{19}$—S—$CH_2$—CH(OH)—$CH_2$—NH—C($C_2H_5$)($C_2H_5$)—C≡CH | | | 1.4888 |
| 23 | tert.-$C_9H_{19}$—S—$CH_2$—CH(OH)—$CH_2$—N(piperazine)N—$CH_2$—CH(OH)—$CH_2$—S(tert.-$C_9H_{19}$) | | | 1.5059 |
| 24 | tert.-$C_9H_{19}$—S—$CH_2$—CH(OH)—$CH_2$—N(piperazine)N—$CH_2$—$CH_2$—OH | | | 1.5102 |
| 25 | (tert.-$C_9H_{19}$—S—$CH_2$—CH(OH)—$CH_2$—)$_2$N—($CH_2$—)$_3$N—($CH_2$—$CH_2$—OH)$_2$ | | | 1.5073 |
| 26 | tert.-$C_9H_{19}$—S—$CH_2$—CH(OH)—$CH_2$—S—(phenyl)—NH—$CH_2$—CH(OH)—$CH_2$—S—tert.-$C_9H_{19}$ | | | 1.5415 |
| 27 | tert.-$C_{12}H_{25}$—S—$CH_2$—CH(OH)—$CH_2$—S—(phenyl)—NH—$CH_2$—CH(OH)—$CH_2$—S—tert.-$C_{12}H_{25}$ | | | 1.5229 |
| 28 | [(tert.-$C_9H_{19}$—S—$CH_2$—CH(OH)—$CH_2$—)$_2$N—$CH_2$—$CH_2$]$_2$S | | | 1.5115 |
| 29 | [(tert.-$C_4H_9$—S—$CH_2$—CH(OH)—$CH_2$—)$_2$N—$CH_2$—$CH_2$]$_2$S | | | 1.5218 |

TABLE 1-continued

| Example No. | Formula | Notes | Boiling point (°C.) | $n_D^{20}$ |
|---|---|---|---|---|
| 30 | tert.-$C_{12}H_{25}$—S—$CH_2$—CH(OH)—$CH_2$—NH—[naphthyl] | | | 1.5472 |
| 31 | tert.-$C_9H_{19}$—S—$CH_2$—CH(OH)—$CH_2$—NH—[phenyl-OH] | | | $n_D^{40}$: 1.5407 |
| 32 | (tert.-$C_4H_9$—S—$CH_2$—CH(OH)—$CH_2$—$)_2$N—$CH_2$—$CH_2$—S—$CH_2$—$CH_2$—OH | | | $n_D^{40}$: 1.5257 |
| 33 | $C_2H_5$—S—$CH_2$—CH(OH)—$CH_2$—NH—[triazole ring] | | 211/0.2 mbar | $n_D^{40}$: 1.5510 |

EXAMPLE 31

Using the Shell four-ball apparatus (IP 239/73 extreme-pressure and wear lubricant test for oils and greases—four-ball machine), the following values ae determined:

1. W.L.=weld load (in Newton (N)). This is the load at which the four balls weld together within 10 seconds.
2. W.S.D.=Wear scar diameter in mm: this is the mean wear diameter under a load of 400N for 1 hour.

The test fluid used for the effectiveness of the additive is a base oil of viscosity ISO-VH 100 and having a low aromatics content and 0.035% of S.

| Additive from Example No. | W.L. (N) | | W.S.D. 1 h (mm) | |
|---|---|---|---|---|
| | 1% of additive | 2.5% of additive | 0.25% of additive | 1.0% of additive |
| 3 | 1850 | 2050 | 0.45 | 0.50 |
| 15 | 1850 | | 0.50 | 0.45 |
| 16 | 1700 | | 0.52 | 0.47 |
| 27 | 2000 | | | 0.50 |

Under these test conditions, the base oil gives a weld load of 1450N and a wear scar diameter of 0.95 mm.

What we claim is:

1. A composition containing a lubricant, a hydraulic fluid or a metal-working fluid none of which are aqueous based on an amount effective to improve the lubricant's or fluid's extreme-pressure and anti-wear properties of at least one compound of the formula $$\left[ R-S-CH_2-\underset{OH}{\underset{|}{CH}}-CH_2-\underset{R^4}{\underset{|}{N}} \right]_n - R^5 \quad (I)$$

wherein n is 1 and R is a radical of the formula $$R^1 - \underset{R^2}{\underset{|}{\overset{R^3}{\underset{|}{C}}}} -$$

in which $R^1$, $R^2$ and $R^3$ independently of one another are $C_1$-$C_{21}$-alkyl and together have not more than 22 carbon atoms, and $R^2$ and $R^3$ can also be hydrogen, or in which R is $C_5$-$C_{12}$-cycloalkyl, $C_7$-$C_9$-aralkyl, unsubstituted or $C_1$-$C_4$-alkyl-substituted phenyl or naphthyl, and in which $R^4$ is hydrogen or $C_1$-$C_{20}$-alkyl which is unsubstituted or substituted by —OH, —$OCH_3$, —CN or —$N(R^6)_2$, and $R^6$ is unsubstituted or OH-substituted $C_1$-$C_4$-alkyl, and $C_1$-$C_{20}$-alkyl, $R^4$ may be interrupted by —O—, —S— or $$-N\hspace{-0.5em}<,$$

or $R^4$ is $C_4$-$C_{20}$-alkenyl, $C_4$-$C_{20}$-alkynyl, unsubstituted or $C_1$-$C_4$-alkyl-substituted $C_6$-$C_{12}$-cycloalkyl, $C_6$-, $C_{10}$-, $C_{14}$-aryl which is unsubstituted or substituted by one or two $C_1$-$C_4$-alkyl or —$CF_3$, one or two OH groups or one or two —$N(R^7)R^8$), and $R^7$ is hydrogen or $C_1$-$C_4$-alkyl and $R^8$ is $C_1$-$C_4$-alkyl or $C_6$- or $C_{10}$-aryl, or in which $R^4$ is anthraquinonyl, or $C_7$-$C_{14}$-aralkyl which is unsubstituted or substituted by —OH, $C_1$-$C_4$-alkoxy or —$N(R^6)_2$ and $R^5$ is $C_4$-$C_{20}$-alkyl which is unsubstituted or substituted by —$OCH_3$, —CN or —$N(R^6)_2$, $R^6$ being as defined above, and which may be interrupted by —O—, —S— or

or $R^5$ is $C_1$-$C_{20}$-alkyl which is substituted by $N(R^6)$(tolyl) or $C_1$-$C_{10}$-heteroaryl, or $R^5$ is unsubstituted $C_4$-$C_{20}$-alkenyl or $C_3$-$C_{20}$-alkenyl substituted by one or more —CN, $C_4$-$C_{20}$-alkynyl, unsubstituted or $C_1$-$C_4$-alkyl-substituted $C_6$-$C_{12}$-cycloalkyl or $C_6$-$C_{10}$- or $C_{14}$-aryl which is unsubstituted or substituted by one or more $C_1$-$C_4$-alkyl groups which may be interrupted by —NH— or —N($R^6$)—, one or more $C_1$-$C_4$-alkoxy, $C_1$-$C_4$-alkylthio and/or OH groups, one or more —$NO_2$, —$CF_3$, and/or —CN, hydroxyethoxy, phenoxy, ureido, carbamoyl, sulfamoyl, benzeneazo, tolueneazo, anilinocarbonyl, anilinosulfonyl, —S—CH$_2$—CH(OH)—$CH_2$—S—R and/or one or two —N($R^7$)($R^8$), $R^7$ and $R^8$ being as defined above and $R^8$ additionally also being acetyl or methoxyphenyl, or in which $R^5$ is anthraquinonyl, hydroxyanthraquinonyl, or $C_7$-$C_{14}$-aralkyl which is unsubstituted or substituted by —OH, one or more $C_1$-$C_4$-alkoxy groups or by —N($R^6$)$_2$, $R^6$ being as defined above, or $R^4$ and $R^5$ together with the N atom to which they are linked form a $C_1$-$C_7$-azacyclic ring which can be aromatic or nonaromatic and may contain one or more N, O or S atoms, the N atom being unsubstituted or substituted by $C_1$-$C_4$-alkyl which in turn can be substituted by —OH, and the $C_1$-$C_7$-azacyclic ring can be unsubstituted or substituted on one C atom by $C_1$-$C_4$-alkyl, =O or =S, or $R^4$ and $R^5$ together with the N atom to which they are linked are 2,2,4-trimethyl-1,2-dihydroquinolyl, a part of a $C_1$-$C_7$-azacyclic divalent to hexavalent ring or a radical of the formulae

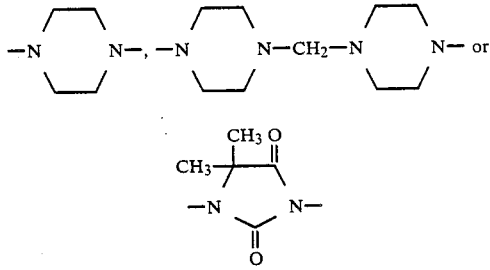

2. A composition according to claim 1, wherein R in the formula I is a radical of the formula

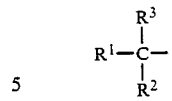

in which $R^1$, $R^2$ and $R^3$ is independently of one another are $C_1$-$C_{18}$-alkyl and do not have more than 22 carbon atoms in total, and $R^2$ and $R^3$ can also be hydrogen, or wherein R is $C_5$-$C_6$-cycloalkyl, benzyl, unsubstituted or $C_1$-$C_4$-alkyl-substituted phenyl or unsubstituted naphthyl.

3. A composition according to claim 2, wherein R in the formula I is a radical of the formula

in which $R^1$, $R^2$ and $R^3$ together with the carbon atom to which they are linked form $C_4$-$C_{16}$-alkyl, in which case none of these substituents $R^1$, $R^2$ and $R^3$ may be hydrogen, or wherein R is cyclohexyl, benzyl, unsubstituted or $C_1$-$C_4$-alkyl-substituted phenyl or unsubstituted naphthyl.

4. A composition according to claim 1 wherein R in the formula I is a radical of the formula

in which $R^1$ is $C_1$-$C_{12}$-alkyl and $R^2$ and $R^3$ are hydrogen.

5. A composition according to claim 1 wherein R in the formula I is a radical of the formula

in which $R^1$ and $R^2$ independently of one another are $C_1$-$C_{12}$-alkyl and together with the carbon atom to which they are linked form $C_3$-$C_{14}$-alkyl and $R^3$ is hydrogen.

6. A method of improving the extreme-pressure and anti-wear properties of a lubricant, a hydraulic fluid or a metal-working fluid none of which are aqueous based comprising the step of adding to said lubricant, hydraulic fluid or metal-working fluid an effective amount of a compound of the formula I according to claim 1.

* * * * *